US008420090B2

(12) United States Patent
Stratilo et al.

(10) Patent No.: US 8,420,090 B2
(45) Date of Patent: Apr. 16, 2013

(54) **RECOMBINANT *B. PSEUDOMALLEI* ADHESIN PROTEIN AND METHODS AND USES THEREOF**

(75) Inventors: Chad Wesley Stratilo, Medicine Hat (CA); Scott James Jager, Dunmore (CA)

(73) Assignee: Her Majesty the Queen in Right of Canada as Represented by the Minister of National Defence, Ottawa (CA)

( * ) Notice: Subject to any disclaimer, the term of this patent is extended or adjusted under 35 U.S.C. 154(b) by 0 days.

(21) Appl. No.: 13/252,677

(22) Filed: Oct. 4, 2011

(65) Prior Publication Data
US 2012/0087924 A1 Apr. 12, 2012

Related U.S. Application Data

(63) Continuation-in-part of application No. 12/509,195, filed on Jul. 24, 2009, now Pat. No. 8,029, 805.

(60) Provisional application No. 61/083,901, filed on Jul. 25, 2008.

(51) Int. Cl.
| | |
|---|---|
| A61K 39/00 | (2006.01) |
| A61K 39/395 | (2006.01) |
| A61K 39/40 | (2006.01) |
| C12N 5/07 | (2010.01) |
| C12P 21/08 | (2006.01) |

(52) U.S. Cl.
USPC .......... 424/139.1; 424/130.1; 424/131.1; 424/150.1; 435/326; 435/327; 435/331; 530/387.1; 530/387.2; 530/387.9

(58) Field of Classification Search .................. None
See application file for complete search history.

(56) References Cited

FOREIGN PATENT DOCUMENTS

| | | |
|---|---|---|
| WO | WO 2004/006857 | 1/2004 |
| WO | WO 2004/113371 | 12/2004 |
| WO | WO 2006/109071 | 10/2006 |
| WO | WO 2007/036735 | 4/2007 |
| WO | WO 2008/140478 | 11/2008 |

OTHER PUBLICATIONS

Bottex et al. Immunopharmacology and Immunotoxicology, 27:565-583, 2005.*
Holden et al. PNAS 101.14240-14245 (2004).
UniProtKB/TrEMBL accession #Q63JIP_BURPS (Oct. 25, 2004).
UniProtKB/TrEMBL accession #Q3JKE3_BURP1 (Nov. 8, 2005).
UniProtKB/TrEMBL accession #A1UZ05_BURMS (Feb. 6, 2007).
Houghten et al (New Approaches to Immunization, Vaccines 86, Cold Spring Harbour Laboratory, p. 21-25, 1986).
Colman et al (Research in Immunology 145: 33-36, 1994).
Greenspan at al, Nature Biotechnology 17:936-937, 1999.
Boddey, J. Molecular and cellular characterisation of *Burkholderia pseudomallei* interactions with host cells. 2005. Thesis submitted in fulfilment of the requirements of the degree of Doctor of Philosophy in the School of Medical Science, Griffith University, Gold Coast, Queensland, ii-iv; 1-32: 224-233.
Low, D. Identification and Functional Analysis of Adhesins Expressed by *Burkholderia pseudomallei*. 2006. The Regents of the University of California.
Whitlock, G. et al. Glanders: off to the races with *Burkholderia pseudomallei*. 2007. FEMS Microbiol Lett 277, 115-122.

* cited by examiner

*Primary Examiner* — Oluwatosin Ogunbiyi
(74) *Attorney, Agent, or Firm* — Santosh K. Chari; Blake, Cassels & Graydon LLP

(57) ABSTRACT

Isolated and/or recombinant adhesin polypeptides from *Burkholderia pseudomallei* are provided, which are used as vaccines. Genetic constructs comprising nucleic acid sequences encoding such polypeptides are also provided. Vectors comprising such constructs have been prepared and used for transforming host cells for producing the polypeptides of the invention. Antibodies to such polypeptides are also provided. Such antibodies can be used to detect the presence of *B. pseudomallei* or *B. mallei* and in methods of treating or preventing *Burkholderia* infection.

11 Claims, 16 Drawing Sheets

GTGAACAGGAACGTGTTTCGTTTGGTGCTGAACAGGGTGGCGGGCATGCCGGTGCCGATGCCGGCGGCGG
AGGTGTCGCGCGGGCGCGGCAAGCTCGGCTGCGGCGGCGTGCGGGCGCAACGTCGCGGCGGTGCGGCGTG
TGCGGCGCTGCTTGGGGTGGCCGGGCCGTCCTTGGCGTTCGCGGCGGTGGTGGCGGACCCGAACGGGGGC
GCGCAGCGGCCCGGCATGGCGACGACGGCGAACGGGACGGACTTGGTCAATATCGTCGCGCCGGACGCGA
CGGGGTTGTCGCACAACAAGTTCAACGAGTTCAGCCCGGTTGGACGCGGCGTGGTGTTGAACAACAGCGT
GCGGCCCGGGGAATCGCAGATCGGCGGCATGGCGGCGCAGAACCCGAACTTGATGCAACCGGCCACCCGG
GCATTGCTCGAGGTGACGCAGCAACGCAGCGTGCTGCAGGGCACGCTGGAGGCGTTCGGCGGCAAGCTCG
ACGTGCTGGTGGCGAACCAGCATGGAGTGACGATCAACGGCTTGACGACGCTGAACGTGGGCCGGCTCGG
CGTGACGACGGGGCAGGTGCTGCCGCAAGCGGCCGGGCAGTTGCGTTTGGGCGTGACGCAAGGCGACGTG
CTGATCGACCATGGGGGCATCGATACCCAGGGCCTGGACATGTTCGACGTGGTGAGCCGCAGCATCGCCG
TGCGCGGGCCGATCCACGATTCGAGCCGCGCCGCGGGCGCCGACGTGCGCCTCGTGGCGGGCGCGACGGC
CTACGATCCGCAGACCGGTCATTATGAGGCGATCGCGGCGGACGAATCGAAGGCGCCGGTGCAGGAGGGA
ATCAGCGGCGAACTGCTGGGAGCGATGCACGGCCGTCACATTGTGCTGGTGAGCACGGAATCGGGCGTGG
GCGTGCGGCCACGACGGACCGATCAAGTCGGCGAACGACATTCGGGTGAGCGCGAACGGCGAGGTGACGCT
GGGCGGGCCGCAGCAGGCGGCTCAGGAGGCGGTTGCAGGAGCGCAGGCGGTAGGCGGCGCCGGCATGCAG
AACGTGATCGCGGGCGGCACGGTGAGCGTCTGCGCGCGTGGGCACGTCGCGATCCAGGGCGCGGTGACCG
CGGGACAGGATGTGGATCTGCAGGGGAAAAGCGTGAAGGCCGGCCGGATGAGCGCGCAGCGCGACGCGCT
GGTGACGGCGGCGGATGGCGTGACGCTCGATGGTCCGGTGGACGCGAAGCGTCACGTGTGGATCGGAGCC
CACGGTGATGTGGTGATCCGTGAAGCGGCGGCGGAGCAGAACGTGGTGCTGCTGGGGCGCAGCGTAACGG
CCGGCCGGTTGGACGCGCAGCGCGACGTATTGGCGGCGGCCCGCGACGGCGTGACGATCCATGAAGCGGC
GGCCGCGGGGCAGGATGTGGTGCTGCAGGGAAGCAGCGCGAGGGTCGGCCAGACGAGCGCGCAGCGCGAT
GTGCTGGTGATGGCGGCAGATGGCGTGACGCTCGATGGGCCGGTGAGCGCGCAGCGCGCCGTATGGGTCG
AGACCCAAGGTGACGTGGCGGGCAGTGAGTGGATCAAGGCCGGACGGGACGTGCAAATCGGCGCGGCGGC
GGATCTGGCGGGCGCGGTAACGGCCGAAGAGATGCAGCAACTCAAGGCCCATGGTGACGCGGCGAACAGG
CGGCGCGTCAAAGCCGGGCGGAACGAGCCAGCCGGCACGGCGGCTGAACGTCCGGCCGCGGCGGAGCAGA
CGGTGGCCGTCGCTGACGCGATGCGCGAGATCGGCGTAGGCGGCGATCGGCTGTCCGGATTGGATGCCGC
GCCGGGTACGCCGGGTACGCCCTTCGGCGCACACCCGCAAGCGATGTTCGACGATCCGGCGGCGCAGATT
GCGCGATCGGCTCGATCCACGGCAACGGCGGGCGGACATGCGGGTTCGTTCATGCGCGTCGGAGACGGTC
ACATCGCCAAAATGACCACGTCCAGAGAGGCGGAGATATACGAGAATTACCGCTTGGCTCTTGCCGGCGT
CATCCCCGACACCGTGCCGCCTGAAGAGGTGGATTCGCGGGTCGGTGTCACGGCCAGGCAGAGGCAGGCC
ATGGCGACTTTCAAAGGGTGGGCGGAGATGAAAGGCCAGCGGGTTGTCGTCATGCAGGCGCTGGGCGCGG
AGATCGCGCCGGAGGACAAGATCGAGCTGGACGTCAAGATCGGCGCCAGTACGGTGTCGCGCACCGAGTT
GATCGGCGCCGGCAGGACTCGCTGGCAGGCCTTGAGCAAGAAGGTGAGATTGACGGCGGCGGACCTGCTG
CGGGGCTCGCGTTCGCTGGTGGGCGACGATCGCGGCTATACGCTCGCCGGCCGCACGAGCGGGGGGATTG
CCCTGGACGCGAGGAATTCACGCAACTCCGTCGGCCGATCCAGCGAATCGCTGATTCGCGAGGCGCTGGA
TCGCTCGCCCGATACGCGCTGGCGGAACGCGCAGCACTTGCTCGGGCAGTTGCAGACCATTCGAGAGAAG
ATGCACGCGTTGCCGCTCACCTTCGTCGCCTCCAGCGTCCTCATTGCAATCGACAAACGGAAACCGGAAA
ACTCGGTCGCCCGGCTGATCGATCTCGCGCACCCGGTGCAGCCTTTCGAAAACGAAGCGGACTATGAGAA
AGTCAATCACCGCTTCGAGGATGGTCTTGACAAGCTGATCAGACTCTTCCAGCAGGTGGAAAAATAG

Figure 1a

MNRNVFRLVLNRVAGMPVPMPAAEVSRGRGKLGCGGVRAQRRGGAACAALLGVAGPSLAFAAVVADPNGG
AQRPGMATTANGTDLVNIVAPDATGLSHNKFNEFSPVGRGVVLNNSVRPGESQIGGMAAQNPNLMQPATR
ALLEVTQQRSVLQGTLEAFGGKLDVLVANQHGVTINGLTTLNVGRLGVTTGQVLPQAAGQLRLGVTQGDV
LIDHGGIDTQGLDMFDVVSRSIAVRGPIHDSSRAAGADVRLVAGATAYDPQTGHYEAIAADESKAPVQEG
ISGELLGAMHGRHIVLVSTESGVGVRHDGPIKSANDIRVSANGEVTLGGPQQAAQEAVAGAQAVGGAGMQ
NVIAGGTVSVCARGHVAIQGAVTAGQDVDLQGKSVKAGRMSAQRDALVTAADGVTLDGPVDAKRHVWIGA
HGDVVIREAAAEQNVVLLGRSVTAGRLDAQRDVLAAARDGVTIHEAAAAGQDVVLQGSSARVGQTSAQRD
VLVMAADGVTLDGPVSAQRAVWVETQGDVAGSEWIKAGRDVQIGAAADLAGAVTAEEMQQLKAHGDAANR
RRVKAGRNEPAGTAAERPAAAEQTVAVADAMREIGVGGDRLSGLDAAPGTPGTPFGAHPQAMFDDPAAQI
ARSARSTATAGGHAGSFMRVGDGHIAKMTTSREAEIYENYRLALAGVIPDTVPPEEVDSRVGVTARQRQA
MATFKGWAEMKGQRVVVMQALGAEIAPEDKIELDVKIGASTVSRTELIGAGRTRWQALSKKVRLTAADLL
RGSRSLVGDDRGYTLAGRTSGGIALDARNSRNSVGRSSESLIREALDRSPDTRWRNAQHLLGQLQTIREK
MHALPLTFVASSVLIAIDKRKPENSVARLIDLAHPVQPFENEADYEKVNHRFEDGLDKLIRLF
QQVEK-

Figure 1b atgaatcacaaagtgcatcatcatcatcatcatatcgaaggtaggcatatggagctcggtacCGGGACGGACTTGGT
CAATATCGTCGCGCCGGACGCGACGGGGTTGTCGCACAACAAGTTCAACGAGTTCAGCCCGGTTGGACGCGGCGTGG
TGTTGAACAACAGCGTGCGGCCCGGGGAATCGCAGATCGGCGGCATGGCGGCGCAGAACCCGAACTTGATGCAACCG
GCCACCCGGGCATTGCTCGAGGTGACGCAGCAACGCAGCGTGCTGCAGGGCACGCTGGAGGCGTTCGGCGGCAAGCT
CGACGTGCTGGTGGCGAACCAGCATGGAGTGACGATCAACGGCTTGACGACGCTGAACGTGGGCCGGCTCGGCGTGA
CGACGGGGCAGGTGCTGCCGCAAGCGGCCGGGCAGTTGCGTTTGGGCGTGACGCAAGGCGACGTGCTGATCGACCAT
GGGGGCATCGATACCCAGGGCCTGGACATGTTCGACGTGGTGAGCCGCAGCATCGCCGTGCGCGGGCCGATCCACGA
TTCGAGCCGCGCCGCGGGCGCCGACGTGCGCCTCGTGGCGGGCGCGACGGCCTACGATCCGCAGACCGGTCATTATG
AGGCGATCGCGGCGGACGAATCGAAGGCGCCGGTGCAGGAGGGAATCAGCGGCGAACTGCTGGGAGCGATGCACGGC
CGTCACATTGTGCTGGTGAGCACGGAATCGGGCGTGGGCGTGCGGCACGACGGACCGATCAAGTCGGCGAACGACAT
TCGGGTGAGCGCGAACGGCGAGGTGACGCTGGGCGGGCCGCAGCGGGCGGCCCAGGAGGCGGTTGCAGGAGCGCAGG
CGGTAGGCGGGGCCGGCATGCAGAACGTGATCGCGGGCGGCACGGTGAGCGTCTGCGCGCGCGGGCACGTCGCGATC
CAGGGCGCGGTGATCGCGGGGCAGGATGTGGATCTGCAGGGGAAAAGCGTGAAGGCCGGCCGGATGAGCGCGCAGCG
CGACGCGCTGGTGACGGCGGCGGATGGCGTGACGCTCGATGGTCCGGTGGACGCCAAGCGTCACGTGTGGATCGGAG
CCCACGGTGATGTGGTGATCCGTGAAGCGGCGGCGGGGCAGAACGTGGTGCTGCTGGGGCGCAGCGTAACGGCCGGC
CGGTTGGACGCGCAGCGCGACGTATTGGCGGCGGCCCGCGACGGCGTGACGATCCATGAAGCGGCAGCCGCGGGGCA
GGATGTGGTGCTGCAGGGAAGCAGCGCGCGGGTCGGCCGGATGAGCGCGCAGCGCGATGTGCTGGTGATGGCGGCAG
ATGGCGTGACGCTCGATGGGCCGGTGAGCGCGCAGCGCGCCGTATGGGTCGAGACCCAAGGTGACGTGGCGGGCAGT
GAGTGGATCAAGGCCGGACGGGACGTGCAAATCGGCGCGGCGGCGGATCTGGCGGGCGCGGTAACGGCCGAAGAGAT
GCAGCAACTCAAGGCCCATGGTGACGCGGCGAACAGGCGGCGCGTCAAAGCCGGGCGGAACGAGCCAGCCGGCGCGG
CGGCTGAACGTCCGGCCGCGGCGGAGCAGACGGTGGCCGTCGCTGACGCGATGCGCGAGATCGGCGTGGGCGGCGAT
CGGCTGTCCGGATTGGATGCCGCGCCGGGTACGCCGGGTACGCCCTTCGGCGCACACCCGCAAGCGATGTTCGACGA
TCCGGCGGCGCAGATTGCGCGATCGGCTCGATCCACGGCAACGGCGGGCGGACATGCGGGTTCGTTCATGCGCGTCG
GAGACGGTCACATCGCCAAAATGACCACGTCCAGAGAGGCGGAGATATACGAGAATTACCGCTTGGCTCTTGCCGGC
GTCATCCCCGACACCGTGCCGCCTGAAGAGGTGGATTGGCGGGTCGGTGTCACGGCCAGGCAGAGGCAGGCCATGGC
GACTTTCAAAGGGTGGGCGGAGATGAAAGGCCAGCGGGTTGTCGTCATGCAGGCGCTGGGCGCGAAGATCGCGCCGG
AGGACAAGATCGAGCTGGACGTCAAGATCGGCGCCAGTACGGTGTCGCGCACCGAGTTGATCGGCGCCGGCAGGACT
CGCTGGCAGGCCTTGAGCAAGAAGGTGAGATTGACGGCGGCGGACCTGCTGCGGGGCTCGCGTTCGTTGGTGGGCGA
CGATCGCGGCTATACGCTCGCCGGCCGCACGAGCGGGGGATTGCCCTGGACGCGAGGAATTCACGCAACTCCGTCG
GCCGATCCAGCGAATCGCTGATTCGCGAGGCGCTGGATCGCTCGCCCGATACGCGCTGGCGGAACGCGCAGCACTTG
CTCGGGCAGTTGCAGACCATTCGAGAGtaggatccgaattcaagcttgtcgacctgcag

Figure 2a

MNHKVHHHHHHIEGRHMELGTGTDLVNIVAPDATGLSHNKFNEFSPVGRGVVLNNSVRPGESQIGGMAAQNPNLMQP
ATRALLEVTQQRSVLQGTLEAFGGKLDVLVANQHGVTINGLTTLNVGRLGVTTGQVLPQAAGQLRLGVTQGDVLIDH
GGIDTQGLDMFDVVSRSIAVRGPIHDSSRAAGADVRLVAGATAYDPQTGHYEAIAADESKAPVQEGISGELLGAMHG
RHIVLVSTESGVGVRHDGPIKSANDIRVSANGEVTLGGPQRAAQEAVAGAQAVGGAGMQNVIAGGTVSVCARGHVAI
QGAVIAGQDVDLQGKSVKAGRMSAQRDALVTAADGVTLDGPVDAKRHVWIGAHGDVVIREAAAGQNVVLLGRSVTAG
RLDAQRDVLAAARDGVTIHEAAAAGQDVVLQGSSARVGRMSAQRDVLVMAADGVTLDGPVSAQRAVWVETQGDVAGS
EWIKAGRDVQIGAAADLAGAVTAEEMQQLKAHGDAANRRRVKAGRNEPAGAAAERPAAAEQTVAVADAMREIGVGGD
RLSGLDAAPGTPGTPFGAHPQAMFDDPAAQIARSARSTATAGGHAGSFMRVGDGHIAKMTTSREAEIYENYRLALAG
VIPDTVPPEEVDWRVGVTARQRQAMATFKGWAEMKGQRVVVMQALGAKIAPEDKIELDVKIGASTVSRTELIGAGRT
RWQALSKKVRLTAADLLRGSRSLVGDDRGYTLAGRTSGGIALDARNSRNSVGRSSESLIREALDRSPDTRWRNAQHL
LGQLQTIRE-

Figure 2b

```
GTGAACAGGAACGTGTTTCGTTTGGTGCTGAACAGGGTGGCGGGCATGCCGGTGCCGATGCCGGCGGCGG
AGGTGTCGCGCGGGCGCGGCAAGCTCGGCTGCGGCGGCGTGCGTGCGCAACGTCGCGGCGGTGCGGCGTG
CGCGGAGCTGCTTGGGGTGGCCGGGCCGTCCTTGGCGTTCGCGGCGGTGGTGGCGGACCCGAACGGGGGC
GCGCAGCGGCCCGGCATGGCGACGACGGCGAACGGGACGGACCTGGTCAATATCGTCGCGCCGGACGCGA
CGGGGTTGTCGCACAACAAGTTCAACGAGTTCAGCCCGGTTGGACGCGGCGTGGTGTTGAACAACAGCGT
GCGGCCCGGGGAATCGCAGATCGGCGGCATGGCGGCGCAGAACCCGAACTTGATGCAACCGGCCACCCGG
GCATTGCTCGAGGTGACGCAGCAACGCAGCGTGCTGCAGGGCACGCTGGAGGCGTTCGGCGGCAAGCTCG
ACGTGCTGGTGGCGAACCAGCATGGAGTGACGATCAACGGCTTGACGACGCTGAACGTGGGCCGGCTCGG
CGTGACGACGGGGCAGGTGCTGCCGCAAGTGGCCGGGCAGTTGCGTTTGGGCGTGACGCAAGGCGACGTG
CTGATCGACCATGGGGGCATCGATACCCAGGGCCTGGATATGTTCGACGTGGTGAGCCGCAGCATCGCCG
TGCGCGGGCCGATCCACGATTCGAGCCGCGCCGCGGGCGCCGACGTGCGCCTCGTGGCGGGCGCGACGGC
CTACGATCCGCAGACCGGTCATTATGAGGCGATCGCGGCGGACGAATCGAAGGCGCCGGTGCAGGAGGGA
ATCAGCGGCGAACTGCTGGGAGCGATGCACGGCCGTCACATTGTGCTGGTGAGCACGGAATCGGGCGTGG
GCGTGCGGCACGACGGACCGATCAAGTCGGCGAACGACATTCGGGTGAGCGCGAACGGCGAGGTGACGCT
GGGCGGGCCGCAGCAGGCGGCTCAGGAGGCGGTTGCAGGAGCGCAGGCGGTAGGCGGCGCCGGCATGCAG
AACGTGATCGCGGGCGGCACGGTGAGCGTCTGCGCGCGTGGGCACGTCGCGATCCAGGGCGCGGTGATCG
CGGGACAGGATGTGGATCTGCAGGGGAAAAGCGTGAAGGCCGGCCGGATGAGCGCGCAGCGCGACGCGCT
GGTGACGGCGGCGGATGGCGTGACGCTCGATGGTCCGGTGGACGCGAAGCGTCACGTGTGGATCGGAGCC
CACGATGATGTGGTGATCCGTGAAGCGGCGGCGGGGCAGAACGTGGTGCTGCTGGGGCGCAGCGTAACGG
CCGGCCGGTTGGACGCGCAGCGCGACGTATTGGCGGCGGCCCGCGACGGCGTGACGATCCATGAAGCGGC
GGCCGCGGGGCAGGATGTGGTGCTGCAGGGAAGCAGCGCGCGGGTCGGCCAGATGAGCGCGCAGCGCGAT
GTGCTGGTGATGGCGGCAGATGGCGTGACGCTCGATGGGCCGGTGAGCGCGCAGCGCGCCGTATGGGTCG
AGACCCAAGGTGACGTGGCGGGCAGTGAGTGGATCAAGGCCGGACGGGACGTGCAAATCGGCGCGGCGGC
GGATCTGGCGGGCGCGGTAACGGCCGAAGAGATGCAGCAACTCAAGGCCCATGGTGACGCGGCGAACAGG
CGGCGCGTCAAAGCCGGGCGGAACGAGCCAGCCGGCACGGCGGCTGAACGTCCCGCCGCGGCGGAGCAGA
CGGTGGCCGTCGCTGACGCGATGCGCGAGATCGGCGTGGGCGGCGATCGGTTGTCCGGATTGGATGCCGC
GCCGGGTACGCCCTTCGGCGCACACCCGCAAGCGATGTTCGACGATCCGGCGGCGCAGATTGCGCGATCG
GCTCGATCCACGGCAACGGCGGGCGGACATGCGGGTTCGTTCATGCGCGTCGGAGACGGTCACATCGCCA
AAATGACCACGTCCAGAGAGGCGGAGATATACGAGAATTACCGCTTGGCTCTTGCCGGCGTCATCCCCGA
CACCGTGCCGCCTGAAGAGGTGGATTGGCGGGTCGGTGTCACGGCCAGGCAGAGGCAGGCCATGGCGACT
TTCAAAGGGTGGGCGGAGATGAAAGGCCAGCGGGTTGTCGTCATGCAGGCGCTGGGCGCGGAGATCGCGC
CGGAGGACAAGATCGAGCTGGACGTCAAGATCGGCGCCAGTACGGTGTCGCGCACCGAGTTGATCGGCGC
CGGCAGGACTCGCTGGCAGGCCTTGAGCAAGAAGGTGAGATTGACGGCGGCGGACCTGCTGCGGGGCTCG
CGTTCGTTGGTGGCGACGATCGCGGCTATACGCTCGCCGGCCGCACGAGCGGGGGGATTGCCCTGGACG
CGAGGAATTCACGCAACTCCGTCGGCCGATCCAGCGAATCGCTGATTCGCGAGGCGCTGGATCGCTCGCC
CGATACGCGCTGGCGGAACGCGCAGCACTTGCTCGGGCAGTTGCAGACCATTCGAGAGAAGATGCACGCG
TTGCCGCTCACCTTCGTCGCCTCCAGCGTCCTCATTGCAATCGACAAACGGAAACCGGAAAACTCGGTCG
CCCGGCTGATCGATCTCGCGCACCCGGTGCAGCCTTTCGAAAACGAAGCGGACTATGAGAAAGTCAATCA
CCGCTTCGAGGATGGTCTTGACAAGCTGATCAGACTCTTCCAGCAGGTGGAAAAATAG
```

Figure 3a

MNRNVFRLVLNRVAGMPVPMPAAEVSRGRGKLGCGGVRAQRRGGAACAELLGVAGPSLAFAAVVADPNGG
AQRPGMATTANGTDLVNIVAPDATGLSHNKFNEFSPVGRGVVLNNSVRPGESQIGGMAAQNPNLMQPATR
ALLEVTQQRSVLQGTLEAFGGKLDVLVANQHGVTINGLTTLNVGRLGVTTGQVLPQVAGQLRLGVTQGDV
LIDHGGIDTQGLDMFDVVSRSIAVRGPIHDSSRAAGADVRLVAGATAYDPQTGHYEAIAADESKAPVQEG
ISGELLGAMHGRHIVLVSTESGVGVRHDGPIKSANDIRVSANGEVTLGGPQQAAQEAVAGAQAVGGAGMQ
NVIAGGTVSVCARGHVAIQGAVIAGQDVDLQGKSVKAGRMSAQRDALVTAADGVTLDGPVDAKRHVWIGA
HDDVVIREAAAGQNVVLLGRSVTAGRLDAQRDVLAAARDGVTIHEAAAAGQDVVLQGSSARVGQMSAQRD
VLVMAADGVTLDGPVSAQRAVWVETQGDVAGSEWIKAGRDVQIGAAADLAGAVTAEEMQQLKAHGDAANR
RRVKAGRNEPAGTAAERPAAAEQTVAVADAMREIGVGGDRLSGLDAAPGTPFGAHPQAMFDDPAAQIARS
ARSTATAGGHAGSFMRVGDGHIAKMTTSREAEIYENYRLALAGVIPDTVPPEEVDWRVGVTARQRQAMAT
FKGWAEMKGQRVVVMQALGAEIAPEDKIELDVKIGASTVSRTELIGAGRTRWQALSKKVRLTAADLLRGS
RSLVGDDRGYTLAGRTSGGIALDARNSRNSVGRSSESLIREALDRSPDTRWRNAQHLLGQLQTIREKMHA
LPLTFVASSVLIAIDKRKPENSVARLIDLAHPVQPFENEADYEKVNHRFEDGLDKLIRLFQQVEK-

Figure 3b

SEQUENCE LISTING

```
<160> NUMBER OF SEQ ID NOS: 12

<210> SEQ ID NO 1
<211> LENGTH: 2727
<212> TYPE: DNA
<213> ORGANISM: Burkholderia pseudomallei

<400> SEQUENCE: 1
gtgaacagga acgtgtttcg tttggtgctg aacagggtgg cgggcatgcc ggtgccgatg      60
ccggcggcgg aggtgtcgcg cgggcgcggc aagctcggct gcggcggcgt gcgggcgcaa     120
cgtcgcggcg gtgcggcgtg tgcggcgctg cttggggtgg ccgggccgtc cttggcgttc     180
gcggcggtgg tggcggaccc gaacgggggc gcgcagcggc ccggcatggc gacgacggcg     240
aacgggacgg acttggtcaa tatcgtcgcg ccggacgcga cggggttgtc gcacaacaag     300
ttcaacgagt tcagcccggt tggacgcggc gtggtgttga acaacagcgt gcggcccggg     360
gaatcgcaga tcgcggcat ggcggcgcag aacccgaact tgatgcaacc ggccacccgg     420
gcattgctcg aggtgacgca gcaacgcagc gtgctgcagg gcacgctgga ggcgttcggc     480
```

```
ggcaagctcg acgtgctggt ggcgaaccag catggagtga cgatcaacgg cttgacgacg        540
ctgaacgtgg gccggctcgg cgtgacgacg gggcaggtgc tgccgcaagc ggccgggcag        600
ttgcgtttgg gcgtgacgca aggcgacgtg ctgatcgacc atgggggcat cgatacccag        660
ggcctggaca tgttcgacgt ggtgagccgc agcatcgccg tgcgcgggcc gatccacgat        720
tcgagccgcg ccgcgggcgc cgacgtgcgc ctcgtggcgg gcgcgacggc ctacgatccg        780
cagaccggtc attatgaggc gatcgcggcg gacgaatcga aggcgccggt gcaggaggga        840
atcagcggcg aactgctggg agcgatgcac ggccgtcaca ttgtgctggt gagcacggaa        900
tcgggcgtgg gcgtgcggca cgacggaccg atcaagtcgg cgaacgacat tcgggtgagc        960
gcgaacggcg aggtgacgct gggcgggccg cagcaggcgg ctcaggaggc ggttgcagga       1020
gcgcaggcgg taggcggcgc cggcatgcag aacgtgatcg cgggcggcac ggtgagcgtc       1080
tgcgcgcgtg ggcacgtcgc gatccagggc gcggtgaccg cgggacagga tgtggatctg       1140
caggggaaaa gcgtgaaggc cggccggatg agcgcgcagc gcgacgcgct ggtgacggcg       1200
gcggatggcg tgacgctcga tggtccggtg gacgcgaagc gtcacgtgtg gatcggagcc       1260
cacggtgatg tggtgatccg tgaagcggcg cggagcagaa acgtggtgct gctggggcgc       1320
agcgtaacgg ccggccggtt ggacgcgcag cgcgacgtat tggcggcggc ccgcgacggc       1380
gtgacgatcc atgaagcggc ggccgcgggg caggatgtgg tgctgcaggg aagcagcgcg       1440
agggtcggcc agacgagcgc gcagcgcgat gtgctggtga tggcggcaga tggcgtgacg       1500
ctcgatgggc cggtgagcgc gcagcgcgcc gtatgggtcg agaccaagg tgacgtggcg       1560 ggcagtgagt ggatcaaggc cggacgggac gtgcaaatcg gcgcggcggc ggatctggcg       1620
ggcgcggtaa cggccgaaga gatgcagcaa ctcaaggccc atggtgacgc ggcgaacagg       1680
cggcgcgtca agccgggcg gaacgagcca gccggcacgg cggctgaacg tccggccgcg       1740
gcggagcaga cggtggccgt cgctgacgcg atgcgcgaga tcggcgtagg cggcgatcgg       1800
ctgtccggat tggatgccgc gccgggtacg ccgggtacgc ccttcggcgc acaccccgcaa       1860 gcgatgttcg acgatccggc ggcgcagatt gcgcgatcgg ctcgatccac ggcaacggcg       1920
ggcggacatg cgggttcgtt catgcgcgtc ggagacggtc acatcgccaa aatgaccacg       1980
tccagagagg cggagatata cgagaattac cgcttggctc ttgccggcgt catccccgac       2040
accgtgccgc ctgaagaggt ggattcgcgg gtcggtgtca cggccaggca gaggcaggcc       2100
atggcgactt tcaaagggtg gcggagatg aaaggccagc gggttgtcgt catgcaggcg       2160
ctgggcgcgc agatcgcgcc ggaggacaag atcgagctgg acgtcaagat cggcgccagt       2220
acggtgtcgc gcaccgagtt gatcggcgcc ggcaggactc gctggcaggc cttgagcaag       2280
aaggtgagat tgacgcggc ggacctgctg cggggctcgc gttcgctggt gggcgacgat       2340
cgcggctata cgctcgccgg ccgcacgagc gggggggattg ccctggacgc gaggaattca       2400
cgcaactccg tcgccgatc cagcgaatcg ctgattcgcg aggcgctgga tcgctcgccc       2460
gatacgcgct ggcggaacgc gcagcacttg ctcgggcagt tgcagaccat tcgagagaag       2520
atgcacgcgt tgccgctcac cttcgtcgcc tccagcgtcc tcattgcaat cgacaaacgg       2580
aaaccggaaa actcggtcgc ccggctgatc gatctcgcgc accccggtgca gcctttcgaa       2640 aacgaagcgg actatgagaa agtcaatcac cgcttcgagg atggtcttga caagctgatc       2700
agactcttcc agcaggtgga aaaatag                                          2727
```

<210> SEQ ID NO 2
<211> LENGTH: 908
<212> TYPE: PRT

-continued

```
<213> ORGANISM: Burkholderia pseudomallei
<220> FEATURE:
<221> NAME/KEY: SIGNAL
<222> LOCATION: (1)..(24)
<223> OTHER INFORMATION: Putative signal sequence

<400> SEQUENCE: 2
```

Met Asn Arg Asn Val Phe Arg Leu Val Leu Asn Arg Val Ala Gly Met
1               5                   10                  15

Pro Val Pro Met Pro Ala Ala Glu Val Ser Arg Gly Arg Gly Lys Leu
            20                  25                  30

Gly Cys Gly Gly Val Arg Ala Gln Arg Arg Gly Gly Ala Ala Cys Ala
        35                  40                  45

Ala Leu Leu Gly Val Ala Gly Pro Ser Leu Ala Phe Ala Ala Val Val
    50                  55                  60

Ala Asp Pro Asn Gly Gly Ala Gln Arg Pro Gly Met Ala Thr Thr Ala
65                  70                  75                  80

Asn Gly Thr Asp Leu Val Asn Ile Val Ala Pro Asp Ala Thr Gly Leu
                85                  90                  95

Ser His Asn Lys Phe Asn Glu Phe Ser Pro Val Gly Arg Gly Val Val
            100                 105                 110

Leu Asn Asn Ser Val Arg Pro Gly Glu Ser Gln Ile Gly Gly Met Ala
        115                 120                 125

Ala Gln Asn Pro Asn Leu Met Gln Pro Ala Thr Arg Ala Leu Leu Glu
    130                 135                 140

Val Thr Gln Gln Arg Ser Val Leu Gln Gly Thr Leu Glu Ala Phe Gly
145                 150                 155                 160

Gly Lys Leu Asp Val Leu Val Ala Asn Gln His Gly Val Thr Ile Asn
                165                 170                 175

Gly Leu Thr Thr Leu Asn Val Gly Arg Leu Gly Val Thr Thr Gly Gln
            180                 185                 190

Val Leu Pro Gln Ala Ala Gly Gln Leu Arg Leu Gly Val Thr Gln Gly
        195                 200                 205

Asp Val Leu Ile Asp His Gly Ile Asp Thr Gln Gly Leu Asp Met
    210                 215                 220

Phe Asp Val Val Ser Arg Ser Ile Ala Val Arg Gly Pro Ile His Asp
225                 230                 235                 240

Ser Ser Arg Ala Ala Gly Ala Asp Val Arg Leu Val Ala Gly Ala Thr
                245                 250                 255

Ala Tyr Asp Pro Gln Thr Gly His Tyr Glu Ala Ile Ala Ala Asp Glu
            260                 265                 270

Ser Lys Ala Pro Val Gln Glu Gly Ile Ser Gly Glu Leu Leu Gly Ala
        275                 280                 285

Met His Gly Arg His Ile Val Leu Val Ser Thr Glu Ser Gly Val Gly
    290                 295                 300

Val Arg His Asp Gly Pro Ile Lys Ser Ala Asn Asp Ile Arg Val Ser
305                 310                 315                 320

Ala Asn Gly Glu Val Thr Leu Gly Gly Pro Gln Gln Ala Ala Gln Glu
                325                 330                 335

Ala Val Ala Gly Ala Gln Ala Val Gly Gly Ala Gly Met Gln Asn Val
            340                 345                 350

Ile Ala Gly Gly Thr Val Ser Val Cys Ala Arg Gly His Val Ala Ile
        355                 360                 365

Gln Gly Ala Val Thr Ala Gly Gln Asp Val Asp Leu Gln Gly Lys Ser
    370                 375                 380

-continued

Val Lys Ala Gly Arg Met Ser Ala Gln Arg Asp Ala Leu Val Thr Ala
385                 390                 395                 400

Ala Asp Gly Val Thr Leu Asp Gly Pro Val Asp Ala Lys Arg His Val
            405                 410                 415

Trp Ile Gly Ala His Gly Asp Val Val Ile Arg Glu Ala Ala Ala Glu
        420                 425                 430

Gln Asn Val Val Leu Leu Gly Arg Ser Val Thr Ala Gly Arg Leu Asp
    435                 440                 445

Ala Gln Arg Asp Val Leu Ala Ala Arg Asp Gly Val Thr Ile His
450                 455                 460

Glu Ala Ala Ala Gly Gln Asp Val Val Leu Gln Gly Ser Ser Ala
465                 470                 475                 480

Arg Val Gly Gln Thr Ser Ala Gln Arg Asp Val Leu Val Met Ala Ala
            485                 490                 495

Asp Gly Val Thr Leu Asp Gly Pro Val Ser Ala Gln Arg Ala Val Trp
            500                 505                 510

Val Glu Thr Gln Gly Asp Val Ala Gly Ser Glu Trp Ile Lys Ala Gly
        515                 520                 525

Arg Asp Val Gln Ile Gly Ala Ala Asp Leu Ala Gly Ala Val Thr
530                 535                 540

Ala Glu Glu Met Gln Gln Leu Lys Ala His Gly Asp Ala Ala Asn Arg
545                 550                 555                 560

Arg Arg Val Lys Ala Gly Arg Asn Glu Pro Ala Gly Thr Ala Ala Glu
            565                 570                 575

Arg Pro Ala Ala Ala Glu Gln Thr Val Ala Val Ala Asp Ala Met Arg
        580                 585                 590

Glu Ile Gly Val Gly Gly Asp Arg Leu Ser Gly Leu Asp Ala Ala Pro
    595                 600                 605

Gly Thr Pro Gly Thr Pro Phe Gly Ala His Pro Gln Ala Met Phe Asp
        610                 615                 620

Asp Pro Ala Ala Gln Ile Ala Arg Ser Ala Arg Ser Thr Ala Thr Ala
625                 630                 635                 640

Gly Gly His Ala Gly Ser Phe Met Arg Val Gly Asp Gly His Ile Ala
            645                 650                 655

Lys Met Thr Thr Ser Arg Glu Ala Glu Ile Tyr Glu Asn Tyr Arg Leu
        660                 665                 670

Ala Leu Ala Gly Val Ile Pro Asp Thr Val Pro Pro Glu Glu Val Asp
    675                 680                 685

Ser Arg Val Gly Val Thr Ala Arg Gln Arg Gln Met Ala Thr Phe
690                 695                 700

Lys Gly Trp Ala Glu Met Lys Gly Gln Arg Val Val Val Met Gln Ala
705                 710                 715                 720

Leu Gly Ala Glu Ile Ala Pro Glu Asp Lys Ile Glu Leu Asp Val Lys
            725                 730                 735

Ile Gly Ala Ser Thr Val Ser Arg Thr Glu Leu Ile Gly Ala Gly Arg
        740                 745                 750

Thr Arg Trp Gln Ala Leu Ser Lys Lys Val Arg Leu Thr Ala Ala Asp
    755                 760                 765

Leu Leu Arg Gly Ser Arg Ser Leu Val Gly Asp Asp Arg Gly Tyr Thr
770                 775                 780

Leu Ala Gly Arg Thr Ser Gly Gly Ile Ala Leu Asp Ala Arg Asn Ser
785                 790                 795                 800

Arg Asn Ser Val Gly Arg Ser Ser Glu Ser Leu Ile Arg Glu Ala Leu
            805                 810                 815

```
Asp Arg Ser Pro Asp Thr Arg Trp Arg Asn Ala Gln His Leu Leu Gly
            820                 825                 830

Gln Leu Gln Thr Ile Arg Glu Lys Met His Ala Leu Pro Leu Thr Phe
        835                 840                 845

Val Ala Ser Ser Val Leu Ile Ala Ile Asp Lys Arg Lys Pro Glu Asn
850                 855                 860

Ser Val Ala Arg Leu Ile Asp Leu Ala His Pro Val Gln Pro Phe Glu
865                 870                 875                 880

Asn Glu Ala Asp Tyr Glu Lys Val Asn His Arg Phe Glu Asp Gly Leu
                885                 890                 895

Asp Lys Leu Ile Arg Leu Phe Gln Gln Val Glu Lys
            900                 905

<210> SEQ ID NO 3
<211> LENGTH: 2369
<212> TYPE: DNA
<213> ORGANISM: Artificial Sequence
<220> FEATURE:
<223> OTHER INFORMATION: Recombinant fusion gene rHlpme

<400> SEQUENCE: 3
atgaatcaca aagtgcatca tcatcatcat catatcgaag gtaggcatat ggagctcggt    60
accgggacgg acttggtcaa tatcgtcgcg ccggacgcga cggggttgtc gcacaacaag   120
ttcaacgagt tcagcccggt tggacgcggc gtggtgttga acaacagcgt gcggcccggg   180
gaatcgcaga tcggcggcat ggcggcgcag aacccgaact tgatgcaacc ggccacccgg   240
gcattgctcg aggtgacgca gcaacgcagc gtgctgcagg gcacgctgga ggcgttcggc   300
ggcaagctcg acgtgctggt ggcgaaccag catggagtga cgatcaacgg cttgacgacg   360
ctgaacgtgg gccggctcgg cgtgacgacg gggcaggtgc tgccgcaagc ggccgggcag   420
ttgcgtttgg gcgtgacgca aggcgacgtg ctgatcgacc atgggggcat cgatacccag   480
ggcctggaca tgttcgacgt ggtgagccgc agcatcgccg tgcgcgggcc gatccacgat   540
tcgagccgcg ccgcgggcgc cgacgtgcgc ctcgtggcgg gcgcgacggc ctacgatccg   600
cagaccggtc attatgaggc gatcgcggcg gacgaatcga aggcgccggt gcaggaggga   660
atcagcggcg aactgctggg agcgatgcac ggccgtcaca ttgtgctggt gagcacggaa   720
tcgggcgtgg gcgtgcggca cgacggaccg atcaagtcgg cgaacgacat tcgggtgagc   780
gcgaacggcg aggtgacgct gggcgggccg cagcgggcgg cccaggaggc ggttgcagga   840
gcgcaggcgg taggcggggc cggcatgcag aacgtgatcg cgggcggcac ggtgagcgtc   900
tgcgcgcgcg gcacgtcgc gatccagggc gcggtgatcg cggggcagga tgtggatctg   960 cagggaaaa gcgtgaaggc cggccggatg agcgcgcagc gcgacgcgct ggtgacggcg  1020
gcggatggcg tgacgctcga tggtccggtg acgccaagcg tcacgtgtg atcggagcc  1080 cacggtgatg tggtgatccg tgaagcggcg cgggggcaga acgtggtgct gctggggcgc  1140
agcgtaacgg ccggccggtt ggacgcgcag cgcgacgtat tggcggcggc ccgcgacggc  1200
gtgacgatcc atgaagcggc agccgcgggg caggatgtgg tgctgcaggg aagcagcgcg  1260
cgggtcggcc ggatgagcgc gcagcgcgat gtgctggtga tggcggcaga tggcgtgacg  1320
ctcgatgggc cggtgagcgc gcagcgcgcc gtatgggtcg agacccaagg tgacgtggcg  1380
ggcagtgagt ggatcaaggc cggacgggac gtgcaaatcg gcgcggcggc ggatctggcg  1440
ggcgcggtaa cggccgaaga gatgcagcaa ctcaaggccc atggtgacgc ggcgaacagg  1500
cggcgcgtca agccgggcg gaacgagcca gccggcgcgg cggctgaacg tccggccgcg  1560
```

```
gcggagcaga cggtggccgt cgctgacgcg atgcgcgaga tcggcgtggg cggcgatcgg   1620
ctgtccggat tggatgccgc gccgggtacg ccgggtacgc ccttcggcgc acacccgcaa   1680
gcgatgttcg acgatccggc ggcgcagatt cgcgcgatcg gctcgatcca cggcaacggcg  1740 ggcggacatg cggcttcgtt catgcgcgtc ggagacggtc acatcgccaa aatgaccacg   1800
tccagagagg cggagatata cgagaattac cgcttggctc ttgccggcgt catccccgac   1860
accgtgccgc ctgaagaggt ggattggcgg gtcggtgtca cggccaggca gaggcaggcc   1920
atggcgactt tcaaagggtg ggcggagatg aaaggccagc gggttgtcgt catgcaggcg   1980
ctgggcgcga agatcgcgcc ggaggacaag atcgagctgg acgtcaagat cggcgccagt   2040
acggtgtcgc gcaccgagtt gatcggcgcc ggcaggactc gctggcaggc cttgagcaag   2100
aaggtgagat tgacggcggc ggacctgctg cggggctcgc gttcgttggt gggcgacgat   2160
cgcggctata cgctcgccgg ccgcacgagc gggggggattg ccctggacgc gaggaattca   2220
cgcaactccg tcggccgatc cagcgaatcg ctgattcgcg aggcgctgga tcgctcgccc   2280
gatacgcgct ggcggaacgc gcagcacttg ctcgggcagt tgcagaccat tcgagagtag   2340
gatccgaatt caagcttgtc gacctgcag                                    2369

<210> SEQ ID NO 4
<211> LENGTH: 779
<212> TYPE: PRT
<213> ORGANISM: Artificial Sequence
<220> FEATURE:
<223> OTHER INFORMATION: Recombinant protein rHlpme

<400> SEQUENCE: 4

Met Asn His Lys Val His His His His His Ile Glu Gly Arg His
1               5                   10                  15

Met Glu Leu Gly Thr Gly Thr Asp Leu Val Asn Ile Val Ala Pro Asp
                20                  25                  30

Ala Thr Gly Leu Ser His Asn Lys Phe Asn Glu Phe Ser Pro Val Gly
            35                  40                  45

Arg Gly Val Val Leu Asn Asn Ser Val Arg Pro Gly Glu Ser Gln Ile
        50                  55                  60

Gly Gly Met Ala Ala Gln Asn Pro Asn Leu Met Gln Pro Ala Thr Arg
65                  70                  75                  80

Ala Leu Leu Glu Val Thr Gln Gln Arg Ser Val Leu Gln Gly Thr Leu
                85                  90                  95

Glu Ala Phe Gly Gly Lys Leu Asp Leu Val Ala Asn Gln His Gly
            100                 105                 110

Val Thr Ile Asn Gly Leu Thr Thr Leu Asn Val Gly Arg Leu Gly Val
        115                 120                 125

Thr Thr Gly Gln Val Leu Pro Gln Ala Ala Gly Gln Leu Arg Leu Gly
    130                 135                 140

Val Thr Gln Gly Asp Val Leu Ile Asp His Gly Ile Asp Thr Gln
145                 150                 155                 160

Gly Leu Asp Met Phe Asp Val Val Ser Arg Ser Ile Ala Val Arg Gly
                165                 170                 175

Pro Ile His Asp Ser Ser Arg Ala Ala Gly Ala Asp Val Arg Leu Val
            180                 185                 190

Ala Gly Ala Thr Ala Tyr Asp Pro Gln Thr Gly His Tyr Glu Ala Ile
        195                 200                 205

Ala Ala Asp Glu Ser Lys Ala Pro Val Gln Glu Gly Ile Ser Gly Glu
    210                 215                 220
```

-continued

```
Leu Leu Gly Ala Met His Gly Arg His Ile Val Leu Val Ser Thr Glu
225                 230                 235                 240

Ser Gly Val Gly Val Arg His Asp Gly Pro Ile Lys Ser Ala Asn Asp
            245                 250                 255

Ile Arg Val Ser Ala Asn Gly Glu Val Thr Leu Gly Gly Pro Gln Arg
            260                 265                 270

Ala Ala Gln Glu Ala Val Ala Gly Ala Gln Val Gly Gly Ala Gly
            275                 280                 285

Met Gln Asn Val Ile Ala Gly Thr Val Ser Val Cys Ala Arg Gly
    290                 295                 300

His Val Ala Ile Gln Gly Ala Val Ile Ala Gly Gln Asp Val Asp Leu
305                 310                 315                 320

Gln Gly Lys Ser Val Lys Ala Gly Arg Met Ser Ala Gln Arg Asp Ala
            325                 330                 335

Leu Val Thr Ala Ala Asp Gly Val Thr Leu Asp Gly Pro Val Asp Ala
            340                 345                 350

Lys Arg His Val Trp Ile Gly Ala His Gly Asp Val Val Ile Arg Glu
            355                 360                 365

Ala Ala Ala Gly Gln Asn Val Val Leu Leu Gly Arg Ser Val Thr Ala
370                 375                 380

Gly Arg Leu Asp Ala Gln Arg Asp Val Leu Ala Ala Arg Asp Gly
385                 390                 395                 400

Val Thr Ile His Glu Ala Ala Ala Gly Gln Asp Val Val Leu Gln
            405                 410                 415

Gly Ser Ser Ala Arg Val Gly Arg Met Ser Ala Gln Arg Asp Val Leu
            420                 425                 430

Val Met Ala Ala Asp Gly Val Thr Leu Asp Gly Pro Val Ser Ala Gln
    435                 440                 445

Arg Ala Val Trp Val Glu Thr Gln Gly Asp Val Ala Gly Ser Glu Trp
    450                 455                 460

Ile Lys Ala Gly Arg Asp Val Gln Ile Gly Ala Ala Ala Asp Leu Ala
465                 470                 475                 480

Gly Ala Val Thr Ala Glu Glu Met Gln Gln Leu Lys Ala His Gly Asp
            485                 490                 495

Ala Ala Asn Arg Arg Arg Val Lys Ala Gly Arg Asn Glu Pro Ala Gly
            500                 505                 510

Ala Ala Ala Glu Arg Pro Ala Ala Glu Gln Thr Val Ala Val Ala
            515                 520                 525

Asp Ala Met Arg Glu Ile Gly Val Gly Gly Asp Arg Leu Ser Gly Leu
            530                 535                 540

Asp Ala Ala Pro Gly Thr Pro Gly Thr Pro Phe Gly Ala His Pro Gln
545                 550                 555                 560

Ala Met Phe Asp Asp Pro Ala Ala Gln Ile Ala Arg Ser Ala Arg Ser
            565                 570                 575

Thr Ala Thr Ala Gly Gly His Ala Gly Ser Phe Met Arg Val Gly Asp
            580                 585                 590

Gly His Ile Ala Lys Met Thr Thr Ser Arg Glu Ala Glu Ile Tyr Glu
            595                 600                 605

Asn Tyr Arg Leu Ala Leu Ala Gly Val Ile Pro Asp Thr Val Pro Pro
            610                 615                 620

Glu Glu Val Asp Trp Arg Val Gly Val Thr Ala Arg Gln Arg Gln Ala
625                 630                 635                 640

Met Ala Thr Phe Lys Gly Trp Ala Glu Met Lys Gly Gln Arg Val Val
```

```
                        645                 650                 655
Val Met Gln Ala Leu Gly Ala Lys Ile Ala Pro Glu Asp Lys Ile Glu
                660                 665                 670

Leu Asp Val Lys Ile Gly Ala Ser Thr Val Ser Arg Thr Glu Leu Ile
            675                 680                 685

Gly Ala Gly Arg Thr Arg Trp Gln Ala Leu Ser Lys Lys Val Arg Leu
        690                 695                 700

Thr Ala Ala Asp Leu Leu Arg Gly Ser Arg Ser Leu Val Gly Asp Asp
705                 710                 715                 720

Arg Gly Tyr Thr Leu Ala Gly Arg Thr Ser Gly Ile Ala Leu Asp
                725                 730                 735

Ala Arg Asn Ser Arg Asn Ser Val Gly Arg Ser Ser Glu Ser Leu Ile
                740                 745                 750

Arg Glu Ala Leu Asp Arg Ser Pro Asp Thr Arg Trp Arg Asn Ala Gln
            755                 760                 765

His Leu Leu Gly Gln Leu Gln Thr Ile Arg Glu
        770                 775

<210> SEQ ID NO 5
<211> LENGTH: 2718
<212> TYPE: DNA
<213> ORGANISM: Burkholderia mallei

<400> SEQUENCE: 5
gtgaacagga acgtgtttcg tttggtgctg aacagggtgg cgggcatgcc ggtgccgatg     60
ccggcggcgg aggtgtcgcg cgggcgcggc aagctcggct gcggcggcgt gcgtgcgcaa    120
cgtcgcggcg gtgcggcgtg cgcggagctg cttggggtgg ccgggccgtc cttggcgttc    180
gcggcggtgg tggcggaccc gaacgggggc gcgcagcggc ccggcatggc gacgacggcg    240
aacgggacgg acctggtcaa tatcgtcgcg ccggacgcga cggggttgtc gcacaacaag    300
ttcaacgagt tcagcccggt tggacgcggc gtggtgttga caacagcgt gcggcccggg     360 gaatcgcaga tcggcggcat ggcggcgcag aacccgaact tgatgcaacc ggccacccgg    420
gcattgctcg aggtgacgca gcaacgcagc gtgctgcagg gcacgctgga ggcgttcggc    480
ggcaagctcg acgtgctggt ggcgaaccag catggagtga cgatcaacgg cttgacgacg    540
ctgaacgtgg gccggctcgg cgtgacgacg ggcaggtgc tgccgcaagt ggccgggcag     600
ttgcgtttgg gcgtgacgca aggcgacgtg ctgatcgacc atgggggcat cgatacccag    660
ggcctggata tgttcgacgt ggtgagccgc agcatcgccg tgcgcgggcc gatccacgat    720
tcgagccgcg ccgcgggcgc cgacgtgcgc ctcgtggcgg gcgcgacggc ctacgatccg    780
cagaccggtc attatgaggc gatcgcggcg acgaatcga aggcgccggt gcaggaggga     840
atcagcggcg aactgctggg agcgatgcac ggccgtcaca ttgtgctggt gagcacggaa    900
tcgggcgtgg gcgtgcggca cgacggaccg atcaagtcgg cgaacgacat tcgggtgagc    960
gcgaacggcg aggtgacgct gggcgggccg cagcaggcgg ctcaggaggc ggttgcagga   1020 gcgcaggcg taggcggcgc cggcatgcag aacgtgatcg cgggcggcac ggtgagcgtc   1080
tgcgcgcgtg ggcacgtcgc gatccagggc gcggtgatcg cgggacagga tgtggatctg   1140
caggggaaaa gcgtgaaggc cggccggatg agcgcgcagc gcgacgcgct ggtgacggcg   1200
gcggatggcg tgacgctcga tggtccggtg gacgcgaagc gtcacgtgtg gatcggagcc   1260
cacgatgatg tggtgatccg tgaagcggcg cggggcaga acgtggtgct gctggggcgc   1320
agcgtaacgg ccggccggtt ggacgcgcag cgcgacgtat tggcggcggc ccgcgacggc   1380
```

```
gtgacgatcc atgaagcggc ggccgcgggg caggatgtgg tgctgcaggg aagcagcgcg    1440
cgggtcggcc agatgagcgc gcagcgcgat gtgctggtga tggcggcaga tggcgtgacg    1500
ctcgatgggc cggtgagcgc gcagcgcgcc gtatgggtcg agacccaagg tgacgtggcg    1560
ggcagtgagt ggatcaaggc cggacgggac gtgcaaatcg cgcggcggc ggatctggcg    1620 ggcgcggtaa cggccgaaga gatgcagcaa ctcaaggccc atggtgacgc ggcgaacagg    1680
cggcgcgtca agccgggcg gaacgagcca gccggcacgg cggctgaacg tcccgccgcg    1740
gcggagcaga cggtggccgt cgctgacgcg atgcgcgaga tcggcgtggg cggcgatcgg    1800
ttgtccggat tggatgccgc gccgggtacg cccttcggcg cacacccgca agcgatgttc    1860
gacgatccgg cggcgcagat tgcgcgatcg gctcgatcca cggcaacggc gggcggacat    1920
gcgggttcgt tcatgcgcgt cggagacggt cacatcgcca aaatgaccac gtccagagag    1980
gcggagatat acgagaatta ccgcttggct cttgccggcg tcatccccga caccgtgccg    2040
cctgaagagg tggattggcg ggtcggtgtc acggccaggc agaggcaggc catggcgact    2100
ttcaaagggt gggcggagat gaaaggccag cgggttgtcg tcatgcaggc gctgggcgcg    2160
gagatcgcgc cggaggacaa gatcgagctg acgtcaaga tcggcgccag tacggtgtcg    2220
cgcaccgagt tgatcggcgc cggcaggact cgctggcagg ccttgagcaa gaaggtgaga    2280 ttgacgcgg cggaccgct gcggggctcg cgttcgttgg tgggcgacga tcgcggctat    2340
acgctcgccg gccgcacgag cggggggatt gccctggacg cgaggaattc acgcaactcc    2400
gtcggccgat ccagcgaatc gctgattcgc gaggcgctgg atcgctcgcc cgatacgcgc    2460
tggcggaacg cgcagcactt gctcgggcag ttgcagacca ttcgagagaa gatgcacgcg    2520
ttgccgctca ccttcgtcgc ctccagcgtc tcattgcaa tcgacaaacg gaaaccggaa    2580
aactcggtcg cccggctgat cgatctcgcg caccggtgc agcctttcga aaacgaagcg    2640
gactatgaga aagtcaatca ccgcttcgag gatggtcttg acaagctgat cagactcttc    2700
cagcaggtgg aaaaatag                                                  2718
```

<210> SEQ ID NO 6
<211> LENGTH: 905
<212> TYPE: PRT
<213> ORGANISM: Burkholderia mallei
<220> FEATURE:
<221> NAME/KEY: SIGNAL
<222> LOCATION: (1)..(24)
<223> OTHER INFORMATION: Putative signal sequence

<400> SEQUENCE: 6

Met Asn Arg Asn Val Phe Arg Leu Val Leu Asn Arg Val Ala Gly Met
1               5                   10                  15

Pro Val Pro Met Pro Ala Ala Glu Val Ser Arg Gly Arg Gly Lys Leu
            20                  25                  30

Gly Cys Gly Gly Val Arg Ala Gln Arg Arg Gly Gly Ala Ala Cys Ala
        35                  40                  45

Glu Leu Leu Gly Val Ala Gly Pro Ser Leu Ala Phe Ala Ala Val Val
    50                  55                  60

Ala Asp Pro Asn Gly Gly Ala Gln Arg Pro Gly Met Ala Thr Thr Ala
65                  70                  75                  80

Asn Gly Thr Asp Leu Val Asn Ile Val Ala Pro Asp Ala Thr Gly Leu
                85                  90                  95

Ser His Asn Lys Phe Asn Glu Phe Ser Pro Val Gly Arg Gly Val Val
            100                 105                 110

Leu Asn Asn Ser Val Arg Pro Gly Glu Ser Gln Ile Gly Gly Met Ala

```
                        115                 120                 125
Ala Gln Asn Pro Asn Leu Met Gln Pro Ala Thr Arg Ala Leu Leu Glu
            130                 135                 140

Val Thr Gln Gln Arg Ser Val Leu Gln Gly Thr Leu Glu Ala Phe Gly
145                 150                 155                 160

Gly Lys Leu Asp Val Leu Val Ala Asn Gln His Gly Val Thr Ile Asn
                165                 170                 175

Gly Leu Thr Thr Leu Asn Val Gly Arg Leu Gly Val Thr Thr Gly Gln
            180                 185                 190

Val Leu Pro Gln Val Ala Gly Gln Leu Arg Leu Gly Val Thr Gln Gly
        195                 200                 205

Asp Val Leu Ile Asp His Gly Gly Ile Asp Thr Gln Gly Leu Asp Met
    210                 215                 220

Phe Asp Val Val Ser Arg Ser Ile Ala Val Arg Gly Pro Ile His Asp
225                 230                 235                 240

Ser Ser Arg Ala Ala Gly Ala Asp Val Arg Leu Val Ala Gly Ala Thr
                245                 250                 255

Ala Tyr Asp Pro Gln Thr Gly His Tyr Glu Ala Ile Ala Ala Asp Glu
            260                 265                 270

Ser Lys Ala Pro Val Gln Glu Gly Ile Ser Gly Glu Leu Leu Gly Ala
        275                 280                 285

Met His Gly Arg His Ile Val Leu Val Ser Thr Glu Ser Gly Val Gly
    290                 295                 300

Val Arg His Asp Gly Pro Ile Lys Ser Ala Asn Asp Ile Arg Val Ser
305                 310                 315                 320

Ala Asn Gly Glu Val Thr Leu Gly Gly Pro Gln Gln Ala Ala Gln Glu
                325                 330                 335

Ala Val Ala Gly Ala Gln Ala Val Gly Ala Gly Met Gln Asn Val
            340                 345                 350

Ile Ala Gly Gly Thr Val Ser Val Cys Ala Arg Gly His Val Ala Ile
        355                 360                 365

Gln Gly Ala Val Ile Ala Gly Gln Asp Val Asp Leu Gln Gly Lys Ser
    370                 375                 380

Val Lys Ala Gly Arg Met Ser Ala Gln Arg Asp Ala Leu Val Thr Ala
385                 390                 395                 400

Ala Asp Gly Val Thr Leu Asp Gly Pro Val Asp Ala Lys Arg His Val
                405                 410                 415

Trp Ile Gly Ala His Asp Asp Val Ile Arg Glu Ala Ala Ala Gly
            420                 425                 430

Gln Asn Val Val Leu Leu Gly Arg Ser Val Thr Ala Gly Arg Leu Asp
        435                 440                 445

Ala Gln Arg Asp Val Leu Ala Ala Arg Asp Gly Val Thr Ile His
    450                 455                 460

Glu Ala Ala Ala Gly Gln Asp Val Val Leu Gln Gly Ser Ser Ala
465                 470                 475                 480

Arg Val Gly Gln Met Ser Ala Gln Arg Asp Val Leu Val Met Ala Ala
                485                 490                 495

Asp Gly Val Thr Leu Asp Gly Pro Val Ser Ala Gln Arg Ala Val Trp
            500                 505                 510

Val Glu Thr Gln Gly Asp Val Ala Gly Ser Glu Trp Ile Lys Ala Gly
        515                 520                 525

Arg Asp Val Gln Ile Gly Ala Ala Asp Leu Ala Gly Ala Val Thr
    530                 535                 540
```

Ala Glu Glu Met Gln Gln Leu Lys Ala His Gly Asp Ala Ala Asn Arg
545                 550                 555                 560

Arg Arg Val Lys Ala Gly Arg Asn Glu Pro Ala Gly Thr Ala Ala Glu
                565                 570                 575

Arg Pro Ala Ala Ala Glu Gln Thr Val Ala Val Ala Asp Ala Met Arg
                580                 585                 590

Glu Ile Gly Val Gly Gly Asp Arg Leu Ser Gly Leu Asp Ala Ala Pro
                595                 600                 605

Gly Thr Pro Phe Gly Ala His Pro Gln Ala Met Phe Asp Asp Pro Ala
610                 615                 620

Ala Gln Ile Ala Arg Ser Ala Arg Ser Thr Ala Thr Ala Gly Gly His
625                 630                 635                 640

Ala Gly Ser Phe Met Arg Val Gly Asp Gly His Ile Ala Lys Met Thr
                645                 650                 655

Thr Ser Arg Glu Ala Glu Ile Tyr Glu Asn Tyr Arg Leu Ala Leu Ala
                660                 665                 670

Gly Val Ile Pro Asp Thr Val Pro Pro Glu Val Asp Trp Arg Val
                675                 680                 685

Gly Val Thr Ala Arg Gln Arg Gln Ala Met Ala Thr Phe Lys Gly Trp
690                 695                 700

Ala Glu Met Lys Gly Gln Arg Val Val Met Gln Ala Leu Gly Ala
705                 710                 715                 720

Glu Ile Ala Pro Glu Asp Lys Ile Glu Leu Asp Val Lys Ile Gly Ala
                725                 730                 735

Ser Thr Val Ser Arg Thr Glu Leu Ile Gly Ala Gly Arg Thr Arg Trp
                740                 745                 750

Gln Ala Leu Ser Lys Lys Val Arg Leu Thr Ala Ala Asp Leu Leu Arg
                755                 760                 765

Gly Ser Arg Ser Leu Val Gly Asp Asp Arg Gly Tyr Thr Leu Ala Gly
770                 775                 780

Arg Thr Ser Gly Gly Ile Ala Leu Asp Ala Arg Asn Ser Arg Asn Ser
785                 790                 795                 800

Val Gly Arg Ser Ser Glu Ser Leu Ile Arg Glu Ala Leu Asp Arg Ser
                805                 810                 815

Pro Asp Thr Arg Trp Arg Asn Ala Gln His Leu Leu Gly Gln Leu Gln
                820                 825                 830

Thr Ile Arg Glu Lys Met His Ala Leu Pro Leu Thr Phe Val Ala Ser
                835                 840                 845

Ser Val Leu Ile Ala Ile Asp Lys Arg Lys Pro Glu Asn Ser Val Ala
850                 855                 860

Arg Leu Ile Asp Leu Ala His Pro Val Gln Pro Phe Glu Asn Glu Ala
865                 870                 875                 880

Asp Tyr Glu Lys Val Asn His Arg Phe Glu Asp Gly Leu Asp Lys Leu
                885                 890                 895

Ile Arg Leu Phe Gln Gln Val Glu Lys
                900                 905

<210> SEQ ID NO 7
<211> LENGTH: 27
<212> TYPE: DNA
<213> ORGANISM: Artificial Sequence
<220> FEATURE:
<223> OTHER INFORMATION: Forward primer

<400> SEQUENCE: 7
catatggtca tgcagaggaa tgaggtc                                27

```
<210> SEQ ID NO 8
<211> LENGTH: 24
<212> TYPE: DNA
<213> ORGANISM: Artificial Sequence
<220> FEATURE:
<223> OTHER INFORMATION: Reverse primer

<400> SEQUENCE: 8
ctcgaggcgt cactcggatg tcct                                           24

<210> SEQ ID NO 9
<211> LENGTH: 33
<212> TYPE: DNA
<213> ORGANISM: Artificial Sequence
<220> FEATURE:
<223> OTHER INFORMATION: Forward primer

<400> SEQUENCE: 9
aaaaaaggta ccgggacgga cttggtcaat atc                                 33

<210> SEQ ID NO 10
<211> LENGTH: 35
<212> TYPE: DNA
<213> ORGANISM: Artificial Sequence
<220> FEATURE:
<223> OTHER INFORMATION: Reverse primer

<400> SEQUENCE: 10 tttttttggat cctactctcg aatggtctgc aactg                              35

<210> SEQ ID NO 11
<211> LENGTH: 27
<212> TYPE: DNA
<213> ORGANISM: Artificial Sequence
<220> FEATURE:
<223> OTHER INFORMATION: Forward primer

<400> SEQUENCE: 11
catatggtca tgcagaggaa tgaggtc                                        27

<210> SEQ ID NO 12
<211> LENGTH: 24
<212> TYPE: DNA
<213> ORGANISM: Artificial Sequence
<220> FEATURE:
<223> OTHER INFORMATION: Reverse primer

<400> SEQUENCE: 12
ctcgaggcgt cactcggatg tcct                                           24
```

RECOMBINANT B. PSEUDOMALLEI ADHESIN PROTEIN AND METHODS AND USES THEREOF

CROSS REFERENCE TO PRIOR APPLICATIONS

The present application is a Continuation in Part of U.S. application Ser. No. 12/509,195, filed on Jul. 24, 2009, now U.S. Pat. No. 8,029,805 issued Oct. 4, 2011, which claims priority under the Paris Convention from U.S. application No. 61/083,901, filed on Jul. 25, 2008. The entire contents of the aforementioned prior applications are incorporated herein by reference.

FIELD OF THE INVENTION

The present invention relates to a recombinant adhesin protein from *Burkholderia* species. In particular, the invention relates to a recombinant adhesin protein from *Burkholderia pseudomallei* and to gene constructs, vectors, transformed host cells, antibodies, and immunogenic compositions associated therewith.

BACKGROUND OF THE INVENTION

*Burkholderia pseudomallei* is a gram negative bacterium that is endemic to much of Southeast Asia and Northern Australia. It is an environmental saprophyte and is the cause of the human disease melioidosis; a severe pulmonary disease with high levels of mortality. In northeast Thailand melioidosis is responsible for at least 20% of all community acquired septicaemias and 40% of sepsis-related mortality. *B. mallei* is closely related to *B. pseudomallei*. It is the causative agent of glanders, a disease that usually affect horses and mules, although it can be highly virulent in humans. Both *B. pseudomallei* and *B. mallei* are considered potential bioweapons and are classified as category B agents by the US Centers for Disease Control and Prevention.

*B. pseudomallei* infections can cause a myriad of symptoms and clinical manifestation of the disease may take decades following exposure. *B. pseudomallei* can invade both phagocytic and non phagocytic cell types employing a type III secretion system or a "molecular syringe" similar to that of *Shigella flexneri*. Once intercellular, *B. pseudomallei* is capable of cell to cell movement via actin based protrusions of the host cell. *B. pseudomallei* adheres to human epithelial cells lines but the mechanism for this adherence is unknown. Multiple type IV pilin genes have been identified in *B pseudomallei*, including a gene encoding the pilus structural protein, PilA. PilA appears to contribute to adherence of *B. pseudomallei* to culture respiratory cell lines and mutants of the gene BPSL0782 have some reduced virulence in BALB/C mice (Essex-Lopresti et al., 2005).

At present there is no effective vaccine that protects against infections by *B. pseudomallei*. A number of virulence factors have been identified in *B. pseudomallei* including a type III secretion system gene cluster, capsular polysaccharides, lipopolysaccharide (LPS), pili and flagella. Several of these have been used in subunit vaccines with very limited success. Attenuated mutants lacking various virulence factors have shown to be protective, although the use of a live attenuated mutant for human vaccination seems highly unlikely.

Preventing the colonization of host cells appears to be the most feasible approach to prevent infection, since once intercellular, *B. pseudomallei* is protected from many of the host immune mechanisms. A critical early stage in bacterial infections is the binding of the pathogenic organism via adhesins to the host receptor molecules. Exploiting bacterial adhesins would appear to be a possible strategy for protection from *B. pseudomallei*.

Glycosaminoglycans form part of the extracellular matrix and are expressed on the surface of all eukaryotic cells. Microbial pathogens bind to proteoglycans, which consist of core proteins covalently linked to glycosaminoglycans or sulphated glycoconjugates. Glycosaminoglycans can be classified into different groups depending on the disaccharide repeat and the overall extent of sulphation: heparin, heparin sulphate, chondroitin-4-sulfate, chondroitin-6-sulfate, dermatan sulphate, and keratan sulphate.

*Bordetella* as well as many other bacterial species utilize filamentous hemagglutinin (FHA) or similar proteins to adhere to sulphated glycoconjugates of respiratory mucus and the cell surfaces of epithelial cells. FHA is an extremely large protein, which is expressed as a 367 kDa precursor protein and processed both at the C and N terminal including cleavage of the C terminal third of the protein resulting in a 220 kDa mature protein. It has several binding domains including a RGD sequence involved in attachment to macrophages and a carbohydrate recognition domain. FHA has a specific glycosaminoglycan-binding or heparin-binding domain that has also been identified in the N-terminal region of the mature FHA. FHA is highly immunogenic and is both surface exposed and secreted. FHA along with inactivated pertussis toxin is a major component of the acellular pertussis vaccine, which is as effective as whole-cell DTP vaccines with fewer side effects.

In order to establish intercellular infections *B. pseudomallei* would require structures that adhere to eukaryotic cells. Identifying proteins that contain domains that have a glycosaminoglycan-binding domain or a heparin binding domain may allow for the identification of essential virulence factors. Generation of this protein or proteins in a recombinant system and using them as part of a subunit vaccine may provide protection from *B pseudomallei*. One such protein candidate is YP_111733, which has been cloned and expressed in a recombinant system. Using this purified protein with adjuvants has shown to be a very effective vaccine against lethal challenge by *B. pseudomallei* Ashdown.

SUMMARY OF THE INVENTION

In one aspect, the present invention provides vaccines consisting of an immunogenic composition comprising the protein YP_111733 or its homolog YP 1077693.1. The protein YP_111733 is encoded by the gene BPSS1727 described further herein. The protein YP 1077693.1 is encoded by the gene BMA10247_A0492 also described further herein.

In another aspect, the invention provides a recombinant vector for producing recombinant proteins for use as a vaccine or as a diagnostic agent.

The invention also provides, in another aspect, a purified protein to be used as a vaccine against or as a diagnostic agent.

In another aspect, the invention provides antibodies that can be used as a diagnostic agent or as a protective therapeutic against.

In another aspect, the present invention provides a vaccine against *B. mallei* and *B. pseudomallei* for the production of a protective immune response.

In particular, the present invention provides, in one aspect, an isolated polynucleotide comprising a nucleic acid sequence selected the group consisting of: SEQ ID NO: 1, SEQ ID NO: 3 and SEQ ID NO: 5.

In another aspect, the invention provides an isolated polypeptide comprising an amino acid sequence having at least 70% identity to a sequence selected from the group consisting of: SEQ ID NO: 2, SEQ ID NO: 4 and SEQ ID NO: 6.

In another aspect, the invention provides an isolated polynucleotide encoding a protein comprising an amino acid sequence having at least 70% identity to a sequence selected from the group consisting of: SEQ ID NO: 2, SEQ ID NO: 4 and SEQ ID NO: 6.

In a further aspect, the invention provides a recombinant DNA construct comprising a DNA fragment having a nucleic acid sequence according to SEQ ID NO: 3, operatively linked to a regulatory sequence.

The invention also provides a vector for the inducible expression of a recombinant protein comprising an amino acid having at least 70% identity to the sequence of SEQ ID NO: 4.

The invention also provides for host cells transformed with the vectors mentioned above and also for methods of producing the recombinant polypeptides of the invention using such transformed cells.

The polypeptides of the invention can incorporated into immunogenic compositions such as vaccines against B. pseudomallei or B. mallei.

BRIEF DESCRIPTION OF THE DRAWINGS

These and other features of the invention will become more apparent in the following detailed description in which reference is made to the appended drawings wherein:

FIGS. 1a and 1b illustrate, respectively, the polynucleotide (SEQ ID NO: 1) and polypeptide (SEQ ID NO: 2) sequences of the gene BPSS1727 and the protein, YP_111733, encoded thereby of B. pseudomallei K96243. The sequence shown with bold underlining (FIG. 1a) reflects the annealing region of oligonucleotide primers used to amplify the gene. The underlined sequence (FIG. 1b) reflects the putative signal sequence of protein.

FIGS. 2a and 2b illustrate, respectively, the polynucleotide (SEQ ID NO: 3) and polypeptide (SEQ ID NO: 4) sequences of the recombinant fusion gene rHlpme and of the plasmid pHLPme which contains an inducible promoter at the 5' start of gene as well as an antibiotic resistance cassette. The amino acid sequence of the recombinant protein rHlpme is also shown. The bolded sequence reflects the sequence from the gene of interest and the underlined sequence represents the polyhistidine tag.

FIGS. 3a and 3b illustrate, respectively, the polynucleotide (SEQ ID NO: 5) and polypeptide (SEQ ID NO: 6) sequences of the gene BMAA1756 and the encoded protein, YP_106315.1, of Burkholderia mallei ATCC 23344. The sequence shown in bold underline reflects the annealing region of oligonucleotide primers used to amplify the gene. The underlined sequence reflects the putative signal sequence of the protein.

FIG. 12a illustrates the sham culture. FIGS. 12b and 12c illustrate cell cultures treated with purified YP_106315.1 protein (SEQ ID NO: 6).

DETAILED DESCRIPTION OF THE INVENTION

Figure 4A:
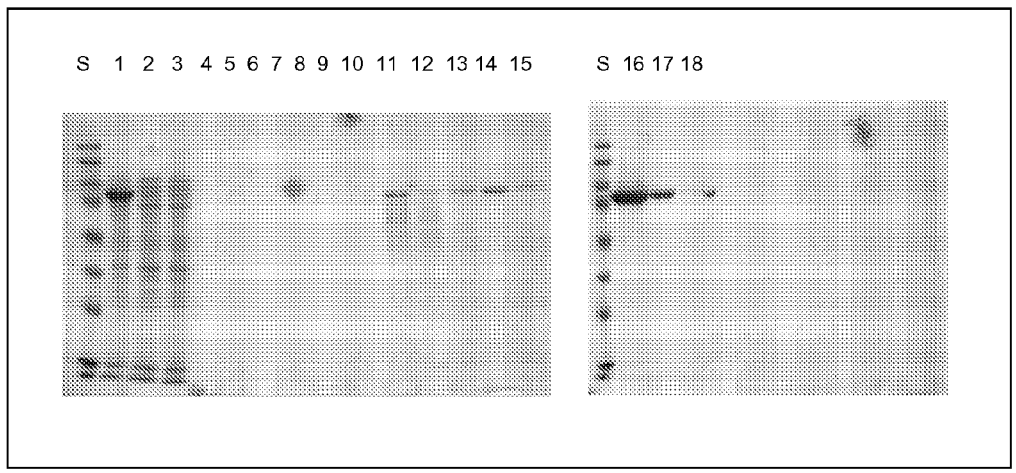
FIG. 4a is a SDS PAGE gel of the purification of the recombinant protein rHlpme.

In the describing the invention, the following terms will be understood as having the following meanings unless stated otherwise:

The term "substantially similar" refers to nucleic acids where a change in one or more nucleotides does not alter the functional properties of the nucleic acid or the encoded polypeptide. Due to the degeneracy of the genetic code, a base pair change can result in no change in the encoded amino acid sequence. For example, the codons ACT, ACC, ACA and ACG all encode a threonine amino acid. Alternatively one or more base pair changes may alter the encoded amino acid however if the substituted amino acid has similar chemical properties functionality of the encoded protein is likely to be unaffected. For example, threonine codons ACT and ACC when changed to AGT or AGC respectively encode for serine, a chemically and biologically similar amino acid. Additionally, certain amino acids within a polypeptide are non essential and alterations may be made in these locations without an effect on the functionality of the polypeptide. The term "substantially similar" refers to polypeptides wherein a change in one or more amino acids does not alter the functional properties of the polypeptide as discussed above.

The terms "sequence identity", "similarity" or "homology" refers to the degree to which two polynucleotide or polypeptide sequences are identical on a residue-by-residue basis over a particular region of comparison. The degree, or percentage of sequence identity, similarity or homology is calculated by comparing two optimally aligned sequences over a region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 70 to 80 percent sequence identity, preferably at least 85 percent identity and often 90 to 95 percent sequence identity, more usually at least 99 percent sequence identity as compared to a reference sequence over a comparison region.

As used herein the term expression vector includes vectors that are designed to provide transcription of a nucleic acid sequence. The transcribed nucleic acid may be translated into a polypeptide or protein product. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication). Other vectors are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors or plant transformation vectors, binary or otherwise, which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. The phrase, "operatively-linked" or "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to include promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990). Regulatory sequences include those that direct constitutive expression of a nucleotide sequence in many types of host cells and those that direct expression of the nucleotide sequence only in certain host cells (e.g., tissue-specific regulatory sequences) or inducible promoters (e.g., induced in response to abiotic factors such as environmental conditions, heat, drought, nutrient status or physiological status of the cell or biotic such as pathogen responsive). Examples of suitable promoters include for example constitutive promoters, ABA inducible promoters, tissue specific promoters and abiotic or biotic inducible promoters. It will be appreciated by those skilled in the art that the design of the expression vector can depend on such factors as the choice of the host cell to be transformed, the level of expression of protein desired as well as timing and location of expression, etc. The expression vectors of the invention can be introduced into host cells to thereby produce proteins or peptides, including fusion proteins or peptides, encoded by nucleic acids as described herein.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell.

A host cell of the invention, such as a prokaryotic or eukaryotic host cell in culture, can be used to produce (i.e., express) a polypeptide of the invention encoded in an open reading frame of a polynucleotide of the invention. Accordingly, the invention further provides methods for producing a polypeptide using the host cells of the invention. In one embodiment, the method comprises culturing the host cell of invention (into which a recombinant expression vector encoding a polypeptide of the invention has been introduced) in a suitable medium such that the polypeptide is produced. In another embodiment, the method further comprises isolating the polypeptide from the medium or the host cell.

In accordance with the present invention, which is described further below, a recombinant fusion protein encompassing the majority of a putative adhesin from *Burkholderia pseudomallei* was produced. The gene (BPSS1727) that expresses this protein in *B. pseudomallei* has been isolated and cloned. A genetic construct has also been made that allows for expression of this protein via an inducible promoter and an amino terminal fusion with a poly His-tag facilitating the purification of the recombinant protein. This purified recombinant protein in conjunction with adjuvants provides protection from lethal challenge by *Burkholderia pseudomallei*. A full length construct of the protein YP_106315.1 has also been created from *B. mallei* 23344 using the gene BMAA1756. This gene (BMAA1756) is nearly identical to BPSS1727. In addition, antibodies to this recombinant protein have been developed. The antibodies have also been found useful for the detection of *B. pseudomallei* and *B. mallei*.

In one aspect, the present invention is directed to a vaccine, in particular a subunit vaccine, to elicit in a mammal an immunogenic response for providing protection against *B. pseudomallei* or *B. mallei* infection. In one aspect, the invention provides a recombinant *Burkholderia* protein (rHlpme) which comprises the majority of the protein YP_111733, which is a hemagglutinin-like protein (HLP) encoded by the gene BPSS1727. This protein is a homolog of the protein YP1077693.1 of *B. mallei*, which is encoded by the gene BMA10247_A0492.

The present invention describes the formation of a genetic or gene construct that encodes a recombinant protein and the production of and purification of this recombinant protein in an *E coli* host system. The recombinant protein, rHlpme, described herein has a length of 779 amino acids, of which 758 amino acids are identical to the protein YP_111733, comprising amino acids 58 to 816 of the mature native *Burkholderia* protein. The recombinant protein is antigenic producing antibodies that react with cultures of *B. mallei* and *B pseudomallei*, specifically identifying a protein of the expected size of the native protein. The recombinant protein, when administered as a recombinant subunit vaccine, is demonstrated to protect mice against a lethal challenge with *B. pseudomallei*.

The genome sequence of *B. pseudomallei* was searched for genes that would code for proteins with hemagglutinin or glycosaminoglycan-binding or heparin binding like domains. A protein identified as Bpse110_02005654 [*Burkholderia pseudomallei* 1106b], a hemagglutinin-like protein (HLP) encoded by the gene BPSS1727, and its homolog *Burkholderia mallei* gene BMA10247_A0492 and protein YP_1077693.1 were identified. The genomes of other sequenced *B. mallei* and *B. pseudomallei* contained genes encoding proteins with 98-100% similarity at the nucleic acid level. A the nucleic acid level BLAST analysis showed 98% homology between sequences of *B. mallei* and *B. pseudomallei* scores were between 4783 and 4935 E values of 0, with 100% coverage of the gene. BLAST analysis of the protein sequences demonstrated E values of 0 and hit scores 1537 to 1476 for *B. mallei* and *B. pseudomallei*. Although many of the proteins identified were classified as hypothetical proteins. It is interesting to note that the start of the proteins different by +/−7 amino acid at the amino terminal end (depending on where the first residue was identified) resulted in a protein of 898 aa for *B. mallei* GB8 to 911 aa for *B. mallei* NCTC 10247. The nucleic acid sequence did not diverge between these strains at the 5' end of the gene, rather differences between the start of the protein were identified. Analysis of the amino acid sequence reveals a putative signal sequence at the amino terminal end of the protein. Comparison of the proteins using the alternative start position shows a mature protein of identical lengths with different signal sequence lengths.

Although the hemagglutinin domain was identified in this protein, it is largely divergent between *B. mallei* and *B. pseudomallei* compared to the hemagglutinin proteins of other bacteria including *Bordetella pertussis*. The protein that showed the most homology to YP_111733 that was not a *Burkholderia pseudomallei* or *B. mallei* protein was FHA of *Bordetella pertussis* Tohama I, which showed 32% amino acids identical at the amino terminal 580 amino acids of the 905 AA of YP_111733 compared to the over 3590 AA of FhaB. Within the hemagglutinin region of this gene there was some similarity to other genetic sequences within the NCBI database. The highest non-*Burkholderia* score was from the genome of *Bordetella avium* where 79 bases were identical out of 109 bases (76% similarity over 3% query coverage) max score of 78.8 with an e value of 1e-10. Bioinfomatic searches showed the gene for a homolog of YP_111733 is deleted in the closely related but non-pathogenic bacterium *B. thailandensis*. This is supported by microarray data of the *B. pseudomallei*, *B mallei* and *B. thailandensis* species showing that the region containing this gene is missing in *B. thailandensis* but found in *B. mallei* and *B. pseudomallei* (Ong et al., 2004).

In one embodiment, the present invention relates to the protein YP_111733, a 94 kDa protein of *B. pseudomallei* encoded by the gene BPSS1727 and its homolog YP1077693.1 of *B. mallei* encoded by the gene BMA10247_A0492. These DNA sequences also include sequences which encode the specific protein epitopes that elicit neutralizing antibody production in animals administered the protein described above or specific peptide epitopes of the aforementioned protein. Specifically this includes all polynucleotide sequences that encode polypeptide sequences that are represented in FIGS. 1*a*, 1*b* and 3*a*, 3*b*.

In another embodiment, the invention relates to recombinant DNA molecules that include any part of the DNA sequences described above and a vector. The vector can be in the form of either prokaryotic or eukaryotic expression vectors with various promoters and selectable markers as will be known to persons skilled in the art.

In one embodiment, the present invention relates to a recombinant protein, rHlpme, which contains 85% of the mature native protein coding sequence including the putative hemagglutinin domain from YP_111733. Such recombinant protein is represented in FIG. 2*b* (SEQ ID NO: 4).

In another embodiment, the present invention relates to host cells that are stably transformed or transfected with the above described recombinant DNA construct. This includes but is not limited to bacteria, lower eukaryotes (yeast), higher eukaryotes or recombinant viruses or naked DNA.

In another embodiment, the present invention relates to genes and nucleic acid sequences present in some *B. pseudomallei* strains that have regions of homology with YP_111733. These genes include: BPSS2053, BURPS1106A_1129, and BURPS1106A_3880, their homologs and their products. These genes or their homologs may or may not be found in all strains of *B. pseudomallei*. These genes code for the proteins YP_112055.1, YP_001065409.1 and YP_001068101.1. These proteins have specific regions of homology with YP_111733. One of these regions encompasses at least the 360 amino terminal amino acids of YP_111733 and shares homology with at least the first 360 amino acids of YP_112055.1, YP_001065409.1 and YP_001068101.1. This amino terminal region appears to be important for the immunological/protective characteristics of YP_111733 against *B. pseudomallei*.

In yet another embodiment, the present invention relates to a method for producing the above recombinant protein, which includes culturing host cells containing the above described vector to induce the production of the recombinant protein and using methods well known in the art to purify the recombinant protein.

In a further embodiment, the present invention relates to the production of antibodies to be used as part of a method for detecting the presence of the *B. pseudomallei* and *B. mallei* in a sample using standard methods common in the art.

In yet another embodiment the present invention relates to the production of antibodies for use in a therapeutic composition for post exposure to *B. pseudomallei* or *B. mallei*.

In another embodiment, the present invention relates to a diagnostic kit which contains the recombinant protein and other reagents (as will be known to persons skilled in the art) for detecting the presence of antibodies to *B. pseudomallei* and *B. mallei*. Such a kit is used to detect, identify or monitor infections by these species.

In another embodiment, the present invention relates to a vaccine that protects against *B. pseudomallei* infection. The vaccine contains, as a major component, a portion of the protein represented in FIG. 1*b* (SEQ ID NO: 2) or the recombinant protein represent in FIG. 2b (SEQ ID NO: 4). The purified proteins and adjuvants are prepared according to methods known in the art.

The invention will now be described with reference to various examples. These examples are intended only to illustrate the invention and are not intended to limit the invention in any way.

EXAMPLE 1

Isolation of Proteins and Production of Recombinant Proteins

Material and Methods a) Development, Synthesis and Cloning of rHLPme

A gene from B. pseudomallei BpSS1727 was PCR amplified on an Eppendorf Mastercycler™ gradient thermocycler using thin wall strip tubes and KOD hot start HiFi polymerase. A typical 25 µl PCR reaction contained 50 ng genomic DNA, 1×KOD buffer, 1.5 mM $MgSO_4$, 0.2 mM dNTP mix, 0.3 uM each of 5' and 3' primers and 0.5 units of KOD HiFi polymerase. Cycling parameters were 95° C. for 2', followed by 30 cycles of 95° C. for 20 mins., 60° C. for 10 mins., 68° C. for 50 mins. and a final extension at 68° C. for 5 mins. Primers used to amplify the entire gene were:

```
                                    (SEQ ID NO: 7)
BpSS1727 5': CATATGGTCATGCAGAGGAATGAGGTC;

(SEQ ID NO: 8)
BPSS1727 3': CTCGAGGCGTCACTCGGATGTCCT.
```

Primers used to amplify the portion of the gene used to produce the recombinant protein were:

```
                                    (SEQ ID NO: 9)
5'HAD: AAA AAA GGT ACC GGG ACG GAC TTG
GTC AAT ATC;

(SEQ ID NO: 10)
CTD3': TTT TTT GGA TCC TAC TCT CGA ATG GTC
TGC AAC TG.
```

The PCR products were purified using a QIAquick™ PCR purification kit following the manufactures instructions. Purified PCR products were digested at 37° C. for 1 hour in 1× buffer G with 10 units each of Kpn I and BamH I (Fermentas). Digested hlp PCR product was purified as above and ligated with 50 ng of similarly digested (KpnI and BamHI) vector DNA (3:1 molar ratio) at 22° C. for 1 hr using standard T4 DNA ligase (Fermentas). 5 µl of each ligation reaction was transformed into 50 µl of chemically competent NovaBlue cells (Novagen). Transformants were screened by PCR (as above) for correct insert size and plasmid DNA from positive clones was isolated using standard alkaline lysis methods (Maniatis) and 70 fmol was sequenced using Beckman Coulter's CEQ DTSC quick start kit (as per manufactures instructions). To clone the entire coding sequence the same procedure was performed except NdeI and Xhoi were used as endonucleases.

b) Production of wssHlpme

An FHA like gene from *B. mallei* was PCR amplified on an Eppendorf Mastercycler™ gradient thermocycler using thin wall strip tubes and KOD hot Start™ HiFi polymerase. A typical 25 µl PCR reaction contained 50 ng genomic DNA, 1×KOD buffer, 1.5 mM $MgSO_4$, 0.2 mM dNTP mix, 0.3 uM each of BPSS1727 5' and BPSS1727 3' primers, 1×Q solution and 0.5 units of KOD HiFi polymerase. Cycling parameters were 95° C. for 2', followed by 30 cycles of 95° C. for 20 mins., 55° C. for 15 mins., 68° C. for 50 mins. and a final extension at 68° C. for 5 mins. The following primers were used for the amplification step:

```
                                   (SEQ ID NO: 11)
Forward WssHlpme primer: CATATGGTCATGCA
GAGGAATGAGGTC;

(SEQ ID NO: 12)
Reverse WssHlpme primer: CTCGAGGCGT
CACTCGGATGTCCT.
```

The PCR products were purified using AMPure™ PCR cleanup kit from Agencourt following the manufactures instructions. Purified PCR products were A-tailed following standard protocols.

Tailed FHA PCR product was T/A cloned into pCRT7/CT-TOPO (Invitrogen) according to manufacturer's instructions. 3 µl of each ligation reaction was transformed into 50 µl of chemically competent NovaBlue cells (Novagen). Transformants were screened by PCR (as above) for correct insert size and plasmid DNA from positive clones was isolated using standard alkaline lysis methods (Maniatis) and 70 fmol was sequenced using Beckman Coulter's CEQ DTSC quick Start™ kit (as per manufactures instructions).

Clones containing the correct sequence were transformed into an *E. coli* expression host and, upon induction, the proteins were expressed as inclusion bodies and/or soluble protein. Inclusion bodies were solubilized with chaotrope and refolded in the presence of osmolytes. FHA protein (soluble and refolded) was purified by Ni chelation chromatography and/or ion exchange chromatography followed by affinity chromatography (heparin column).

c) Production and Solubilization of the Recombinant Protein

Clones containing the correct sequence were transformed into an *E. coli* expression host. Single colonies were grown in liquid LB and at OD600. Expression of the recombinant protein was induced using 1 mM IPTG. The recombinant protein was produced as inclusion bodies and/or soluble protein. Inclusion bodies were solubilized using 8 M urea, 50 mM Tris (pH of 8), 5 mM BME and 10 mM imidazole. The suspension was incubated for 30 minutes at room temperature then centrifuged to clear any insoluble material for 10 minutes at 8K rcf (relative centrifugal force).

d) Polyclonal Antisera Generation

Groups of five female 5- to 6-week-old BALB/c mice were immunized with the purified recombinant rHlpme protein, which was given with Titremax™ gold adjuvant. The proteins were prepared for immunization at a concentration of 400 µg/ml in PBS mixed 1:1 with Titremax™ gold. The proteins were delivered by intraperitoneal (i.p.) injection of 100 µl of each protein (20 ug) in adjuvant on days 0, 14, and 28. Blood was collected by tail vein on day 21. On day 42 mice were exsanguinated via cardiac puncture. Sera were separated from red blood cells via centrifugation. The sera were used neat or the polyclonal antibodies were purified using protein G™ columns in accordance with the manufacturer's directions (GE Healthcare).

e) Elisa

Elisas were preformed via the indirect method. The antigen was either purified rHlpme or live *B. mallei* 23344 or *B. pseudomallei* (clinical isolate) in PBS. Wells were washed (PBS+T, 0.05% Tween 20) and blocked 2% BSA in PBS. The primary antibody was polyclonal antisera (dilute or neat)

from mice, produced as described above. Wells were washed (PBS+T) again. The secondary antibody was antimouse HRP conjugate. Wells were washed (PBS+T) again. Antibodies were detected and quantified using a colorimetric assay (ABTS substrate read at 405 nm).

f) SDS-PAGE and Western Blotting

Proteins were resolved on 10% SDS-polyacrylamide gel (Laemmli, U.K., Nature, 1970, 227:680-685). Samples were boiled for 5 minutes prior to application to the gel. Proteins were blotted onto nitrocellulose paper using a wet or semi-dry apparatus (Biorad) as recommended by the manufacturer. Following protein transfer, the nitrocellulose was blocked for 30 minutes in PBS containing 5% skimmed milk powder and 0.05% Tween-20™. The nitrocellulose was then incubated in PBS containing 5% skimmed milk powder and 0.05% Tween-20™ and 1:1000 purified IgG from mice vaccinated with rHLPme 2× with adjuvant. Membranes were washed 5× in PBST and incubated with HRP-conjugated goat anti-mouse IgG 1:5000 for 1 hour and washed 5× with PBST and finally incubated for 3 minutes in SuperSignal™ West pico substrate (Pierce).

g) Purification of Recombinant Protein

Recombinant HLPme was purified by Ni chelation chromatography under denaturing conditions as described by the manufacturer (Qiagen). The inclusion bodies that had been solubilized in 8 M urea, 50 mM Tris pH 8, 5 mM BME and 10 mM Imidazole, was applied to a NTA column. The column was washed with the above buffer until absorbance 280 nm returned to background levels. Matrix assisted refolding was performed, whereby the denaturing buffer was replaced over a 100 ml gradient with 50 mM Tris pH 8, 300 mM NaCl, 50 mM urea, 0.1% OGP and 10 mM Imidazole. The refolded protein was eluted with a 50 ml gradient of Imidazole (10 mM to 500 mM) in a buffer containing 50 mM Tris pH8, 300 mM NaCl, 1.0% OGP. The column was washed with 8M urea pH 4.4 to elute protein that was not soluble in primary elution. The protein eluted in 8M urea pH 4.4 was dialyzed against PBS and 0.018% n-Dodecyl B-D maltoside in a step down fashion (6, 4, 2, 0 M urea).

h) Mouse Immunization and Challenge

The purified protein was used with or without adjuvant as a vaccine against *B. pseudomallei* Ashdown. To test the immunogenicity and protection offered by this protein, the ~15-20 ug of rHlpme with adjuvant (TiterMax™ gold) was administered i.p. or subcutaneously (s.c.) to 20 g BALB/c mice. The mice were boosted 21 days post vaccination. Twenty-one days subsequent to the boost, the animals were challenged i.n. with ~4.0E3 of *B. pseudomallei* Ashdown.

Results

The gene, BPSS1727 (FIG. 1), cloned from *B. pseudomallei* is conserved between *B. pseudomallei* and *B. mallei* but is not conserved with other members of the *Burkholderia* genus or with more distantly related bacteria.

Figure 4B:
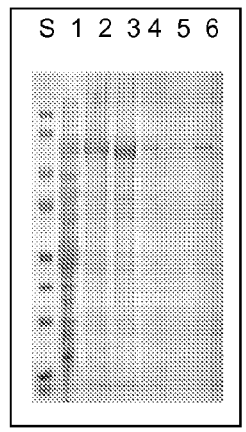
FIG. 4b is a SDS PAGE gel of the purification of the recombinant protein WssHlpme.
Figure 5:
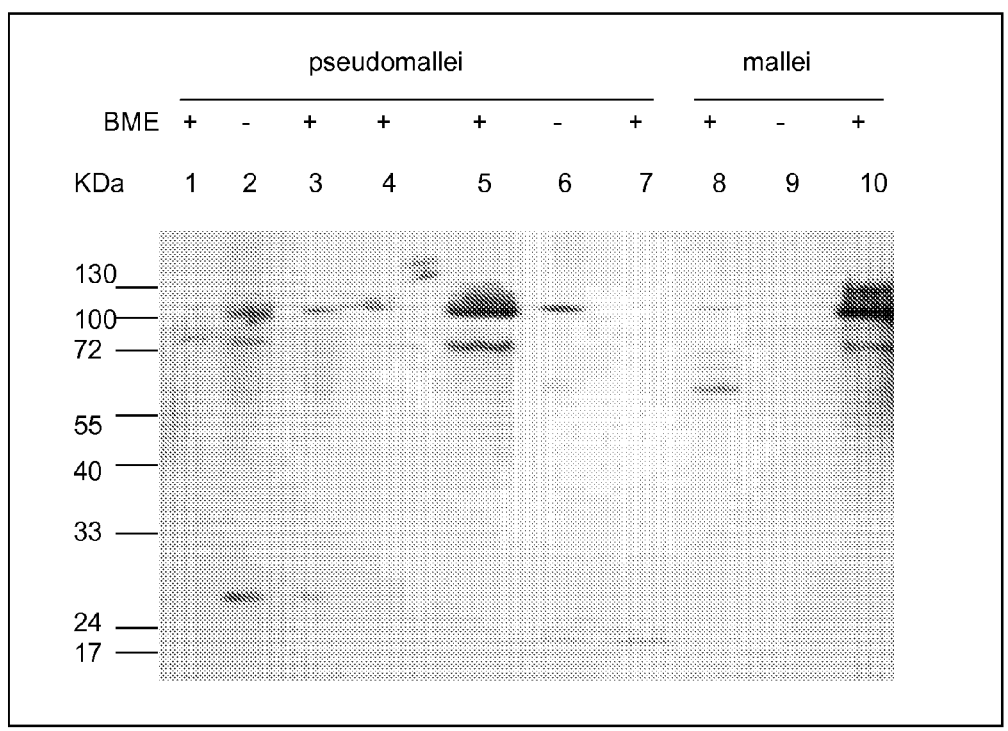
FIG. 5 is a Western blot analysis of polyclonal antibodies produced against the recombinant protein rHlpme.
Figure 6:
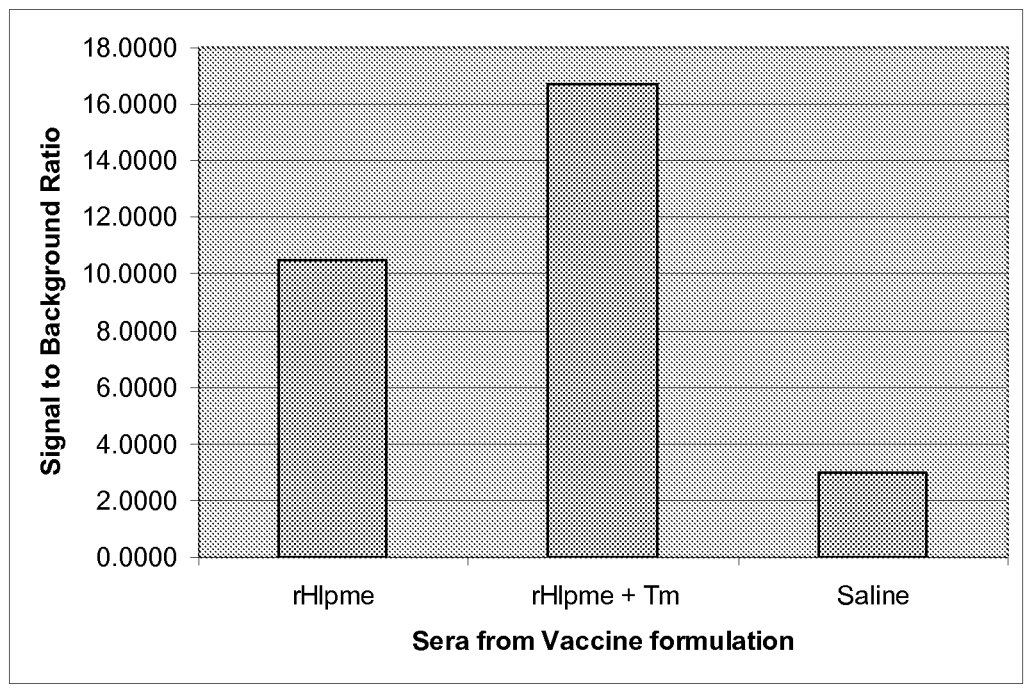
FIG. 6 illustrates the specific identification of the recombinant protein rHlpme by the polyclonal sera from mice vaccinated with the recombinant protein rHlpme (with or without the adjuvant TiterMax™ gold).
Figure 7:
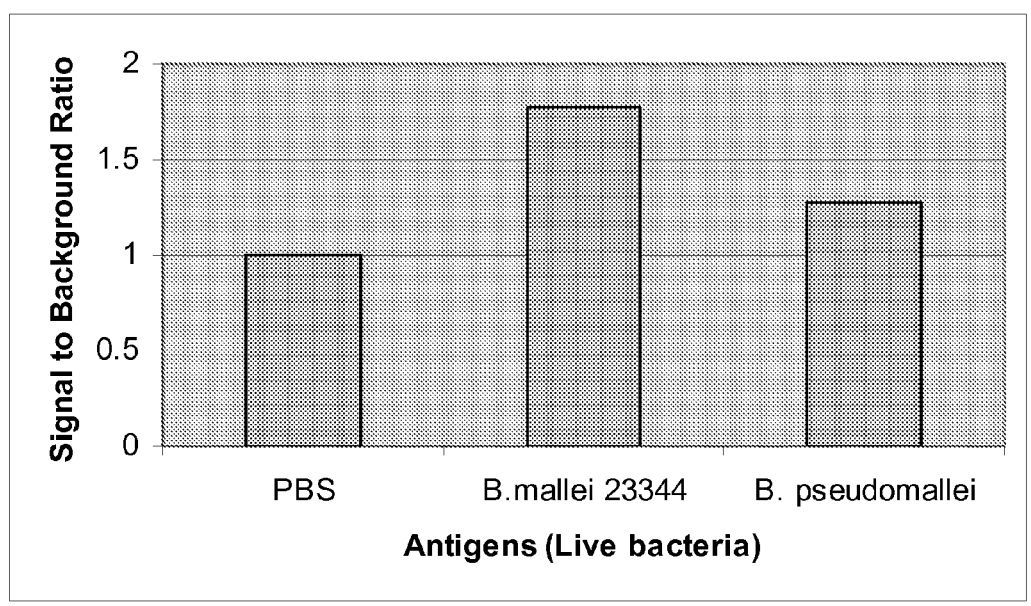
FIG. 7 illustrates the specific identification of B. mallei and B pseudomallei using polyclonal sera from mice vaccinated with the recombinant protein rHlpme.

The gene encoding this protein was cloned (FIG. 1) and expressed in a recombinant form (FIG. 2) in *E. coli*. The gene cloned from *B. pseudomallei* is highly conserved in *B. mallei* (FIG. 3). The recombinant protein was expressed using a plasmid with an inducible promoter. A protein of the expected size of 81 kDa was produced. The recombinant protein was purified using NTA chromatography (FIG. 4). The recombinant protein was used as an immunogen and polyclonal antibodies were generated against it. The purified antibodies were used to identify the native protein in cultures of *B. mallei* and *B. pseudomallei* (FIG. 5). Thus, such antibodies serve to identify or detect the presence of *B. mallei* and *B. pseudomallei*. The recombinant protein was specifically identified using polyclonal sera from mice vaccinated with the recombinant protein rHlpme (FIG. 6). The polyclonal serum was also used in an Elisa to identify live *B. mallei* and *B. pseudomallei* (FIG. 7).

A second recombinant protein that expresses the full length protein from *B. mallei* 23344 was also produced. This construct, WssHlpme, produces the full length protein with the signal sequence. Upon inducing expression of this construct, the protein produced is of the expected size (FIG. 4b).

Figure 8:
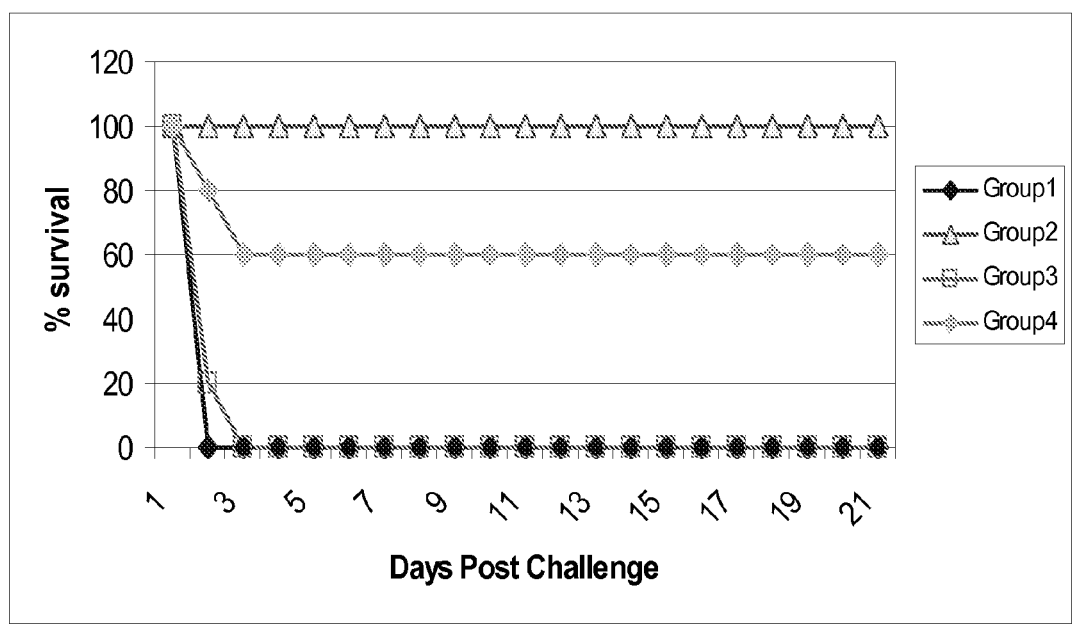
FIG. 8 illustrates the protective immune response against B pseudomallei by mice vaccinated with the recombinant protein rHlpme.
Figure 9:
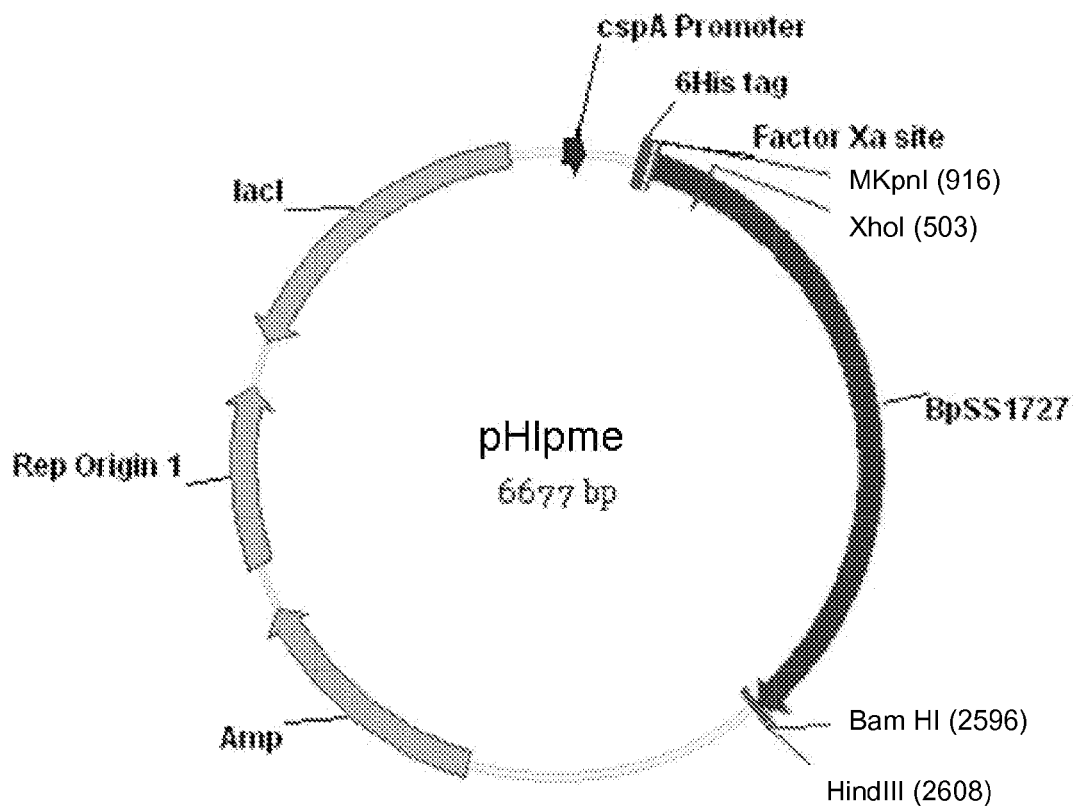
FIG. 9 is a vector map of the plasmid pHlpme, which contains the polynucleotide sequences of the recombinant fusion gene rHlpme. The plasmid contains an inducible promoter 5' of the start of the gene as well as an antibiotic resistance cassette. The recombinant gene contains part of the B. pseudomallei gene BPSS1727 as shown in FIG. 2.
Figure 10:
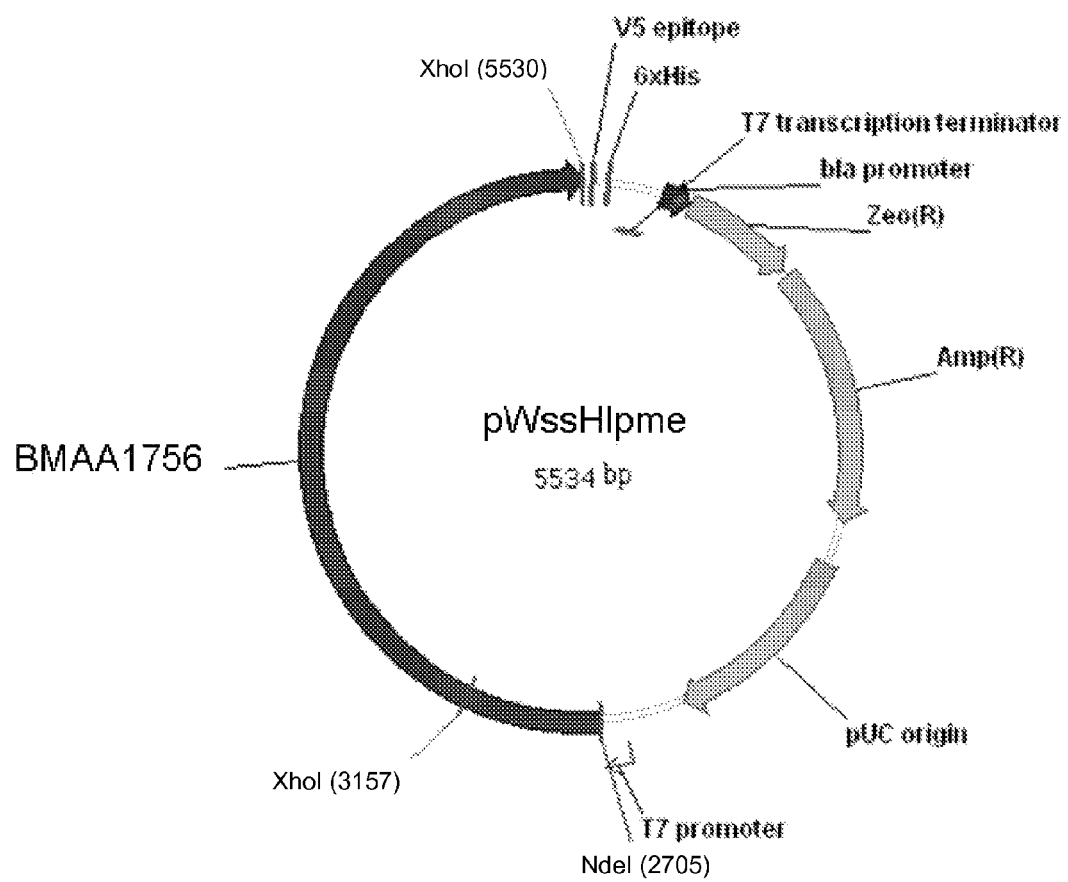
FIG. 10 is a vector map of the plasmid pwssHlpme, which contains the polynucleotide sequences of the recombinant fusion gene wsshlpme. The plasmid contains an inducible promoter 5' of the start of the gene as well as an antibiotic resistance cassette. The protein produced is the full length protein including the signal sequence of the protein encoded by gene BMAA1756 as shown in FIG. 3.

The recombinant protein (rHlpme) was used as a component in a vaccine along with adjuvants and administered both i.p. and s.c. to groups of mice and boosted 21 days post vaccination. Twenty-one days post boost, the mice were challenged with 5E3 CFUs of *B. pseudomallei*. The vaccinated mice with adjuvants were protected (FIG. 8) while control mice succumbed to infection within 3 days. The rHLPme protein, when administered i.p. with an adjuvant such as TiterMax™ gold, offered complete protection from *B. pseudomallei*.

Discussion

The recombinant protein rHlpme identified in FIG. 2 was used as part of a vaccine against *B. pseudomallei*. Mice vaccinated with this vaccine were protected against lethal challenge by *B. pseudomallei*. This protein is conserved within *B. pseudomallei* and *B. mallei* but is not found in other *Burkholderia* strains. Members of the *Burkholderia* genus have several proteins that are described as hemagglutinin or hemagglutinin-like proteins, including YP_112055.1, YP_001065409.1 and YP_001068101.1. BLAST analysis shows that these proteins share homology with YP_111733 (encoded by the gene BPSS1727). These proteins share a conserved region with the amino terminal of YP_111733. The 338 amino terminal amino acids of YP_111733 have homology (with 48% positive residues) to YP_112055.1 and similar levels of homology with the other hemagglutinins of *B. pseudomalleil* (YP_001065409.1 and YP_001068101.1). Hemagglutinin-like proteins are also found in other *Burkholderia* species including *B. thailandensis*, *B. xenovorans*, *B. phymatum*, *B. vietnamiensis*, *B. dolosa* and *B. cepacia*. A 373 amino acid protein described as a hemaglutinin domain protein (YP_105472, *B. mallei* ATCC 23344) has been identified in *B. mallei*. This protein has no significant similarity to the protein described herein.

Although FhaB has been used in *Bordetella pertussis* acellular vaccines, the protein rHlpme described above is very divergent from FhaB as it shares limited homology and is much smaller. The only conserved domain, the hemagglutinin domain, is poorly conserved between the *Bordetella* and *Burkholderia*, perhaps due to differences in life histories. Thus, the polypeptides and polynucleotides described above appear to be unique and previously unexploited.

On the basis of the above detailed description, various conclusions can be drawn with respect to the utility of the present invention. Firstly, the isolated and/or recombinant polypeptides of the present invention are useful as vaccine candidates for *B. pseudomallei* or *B. mallei* or in an immunogenic composition comprising the above mentioned recombinant protein and other components. It will also be understood that such other component may be a further immunogenic component isolated from a microorganism or one that is chemically synthesized. Such components may comprise any suitable or pharmaceutically acceptable carriers, excipients, diluents etc.

It will be understood that the polypeptides according to the present invention may have at least 70% sequence identity to the sequences shown herein. In one aspect, such sequence identity is at least 75% or at least 80% or at least 85% or at least 90% or at least 95% or at least 99% or at least 100%.

The recombinant proteins according to the invention may be produced in soluble or insoluble, such as in the form of inclusions bodies. In the latter case, the recombinant protein may be solubilized as needed.

According to the invention, a recombinant vector, such as an expression vector, may be produced containing all or part of the isolated and/or recombinant polynucleotides described above. The invention also provides recombinant host cells, transformed with such vectors, and incorporating at least one of the polynucleotides described above. The above mentioned polypeptides can therefore be produced through expression by such recombinant host cells. The expressed proteins may comprise fusion proteins or native proteins.

According one aspect of the invention, antibodies, such as polyclonal antibodies, are provided for one or more epitopes of the polypeptides described above. The isolated and/or recombinant polynucleotides of the invention or epitopic fragments thereof can be utilized as in vitro agents for producing such antibodies. It will also be understood that such antibodies may be used in passive immune therapy against *B. pseudomallei* or *B. mallei* infection.

The polynucleotides and polypeptides described herein may be useful as in vitro agents for diagnostic and screening procedures for the presence of *B. pseudomallei* or *B. mallei* in a sample. In one aspect, the antibodies to the isolated and/or recombinant polypeptides described above, or epitopic fragments thereof, can be used in an immunoassay for detecting the presence of *B. pseudomallei* or *B. mallei* in a sample.

In a further embodiment, the isolated and/or recombinant polynucleotides of the invention, or epitopic fragments thereof, can be used as reagents in the screening or testing pharmaceutical agents or compounds which reduce or eliminate virulence of *B. pseudomallei* or *B. mallei*. In such method, the isolated and/or recombinant polypeptides described above, or an epitopic fragment thereof, is assayed.

EXAMPLE 2

Further Characterization of Proteins

Materials and Methods
a) Bacterial Strains and Growth Conditions

*B. pseudomallei* was grown at 37° C. on LB agar or in LB broth. All manipulations with *B. pseudomallei* were carried out in class II microbiological safety cabinets located in designated bio safety level 3 (BSL-3) laboratories. LB broth with various levels of NaCl was used to assess the expression of the protein in *Burkholderia* in culture media. NaCl concentrations used were, 160 and 320 mM in the liquid media.

b) Animal Work

Groups of five female 5- to 6-week-old BALB/c mice were challenged intranasally with approximately 50 $Ld_{50}$ of *Burkholderia pseudomallei* K96243. When the animals were showing clinical signs of infection the animals were euthanized and liver, lungs, spleen, and brain were collected and homogenized. The samples were then used for analysis via SDS-page and western blot as described above.

c) Purification of Peptide with Heparin Resin

Recombinant Hlpme was purified by affinity chromatography on a heparin sepharose 6 fast flow column (GE Healthcare). Inclusion bodies that had been solubilized in a solution of 8M urea, 100 mM Tris, 100 mM $NaH_2PO_4$, 0.05% Tween 20, 1 mM DTT, pH 9.9 were diluted 1:10 in refolding buffer (20 mM tris pH 7.5, 0.5 mM arginine, 1 mM DTT, 1 mM dodecylmaltoside) and stirred rapidly for 30 minutes. Heparin sepharose 6 F.F. (fast flow) resin (equilibrated in refolding buffer) was then added and the slurry was incubated for 30 minutes at room temperature. The slurry was transferred to a polypropylene column and washed with 20 mM tris pH 7.5, 1 mM DTT, 1 mM dodecylmaltoside until absorbance at 280 nm returned to background levels. Purified protein was eluted with a NaCl step gradient (300 mM, 500 mM, 1.0M) in the above buffer.

Figure 11:
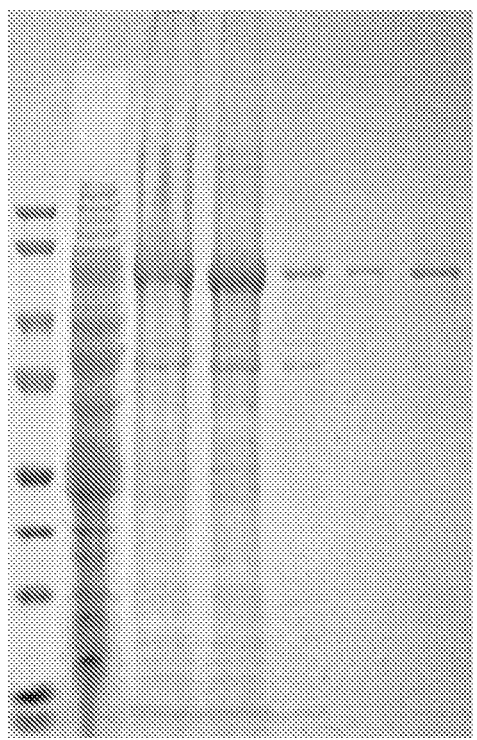
FIG. 11 illustrates the purification of peptides using heparin resin as discussed in Example 2.

FIG. 11 illustrates the above purification. In FIG. 11, lane 1=PageRuler MWM; lane 2=soluble BugBuster lysate; lane 3=insoluble BugBuster lysate; lane 4=heparin column flow through; lane 5=column washes; lane 6=0.3M NaCl elution; and, lane 7=1.5M NaCl elution.

d) Cell Culture

In this study, RAW 267 cells were incubated for 24 hours in culture media with 35 ng/ml of purified recombinant protein or a sham. Murine macrophage cell line RAW 264.7 was obtained from the American Type Culture Collection (ATCC, Rockville, Md.). Cells were maintained in Dulbecco's Modified Eagle's Medium (DMEM) (Invitrogen) supplemented with 10% (vol/vol) heat-inactivated fetal bovine serum (Invitrogen) at 37° C. under an atmosphere containing 5% $CO_2$. For macrophage assays, RAW 264.7 cells were re-suspended in DMEM supplemented with fetal bovine serum (DMEM-10), transferred into 6-well tissue culture plates containing coverslips, and incubated overnight. Confluent monolayers of Raw267 macrophages on glass coverslips were treated with purified protein (obtained from the procedure described above) in DMEM for 12-24 hours. Coverslips were then washed in sterile 1×PBS before fixing with 4% paraformaldehyde (w/v) in PBS for 15 min. Coverslips were then washed in 1×PBS. Macrophages were permeabilised by covering with 0.2% Triton X-100 in 1 PBS for 15 minutes. Anti-fade mounting solution (with DAPI (Invitrogen)) was used to mount the cells. Staining of the filamentous actin cytoskeleton was carried out with Alexa Fluor® 488 phalloidin (Invitrogen) at a 1/500 dilution in 1×PBS by inverting the coverslip onto a 60 µl drop of the staining solution and incubating at room temperature in the dark for 1 h. Following incubation the coverslips were washed 2×5 minutes in 1×PBS before visualization using fluorescence microscopy.

Figure 12A:
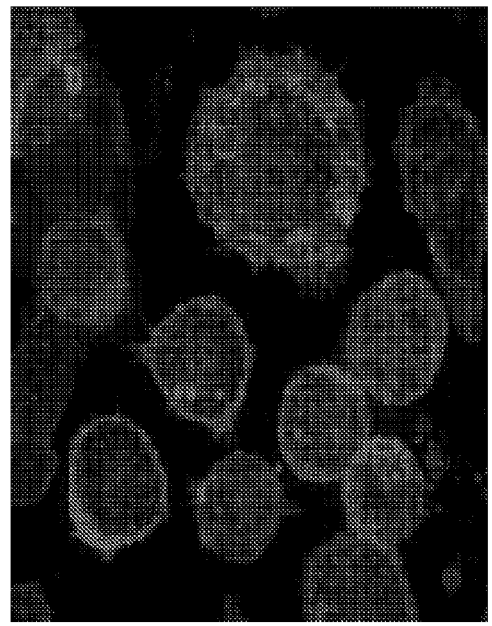
FIGS. 12a to 12c illustrate cell cultures of Example 2.
Figure 12B:
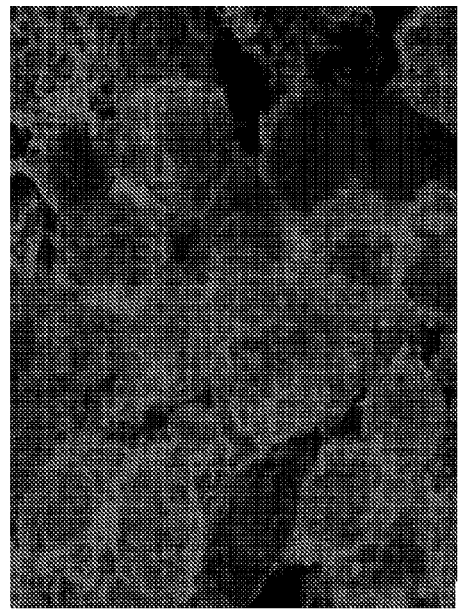
Figure 12C:
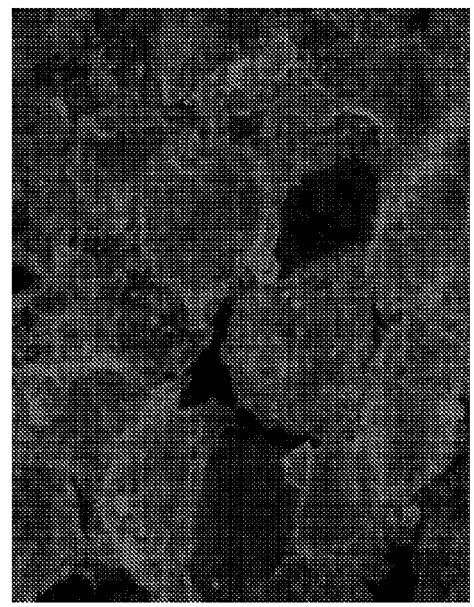

FIGS. 12a to 12c illustrate the above cell culturing. FIG. 12a illustrates sham treated Raw 267 cells. FIGS. 12b and 12c illustrate cells treated with the purified peptide YP_106315.1, of *Burkholderia mallei* ATCC 23344 (SEQ ID NO: 6).

Results and Discussion

As shown in FIG. 1, the recombinant protein rHlpme (SEQ ID NO: 4) and protein YP_106315.1 (SEQ ID NO: 6) (i.e. recombinant protein from *B. mallei* that is expressed in *E. coli*) both demonstrated heparin binding activity. This was found to be a novel feature of both proteins. The heparin binding found in this study suggests a possible mechanism that such proteins (SEQ ID NOs: 4 and 6) adhere to cell surfaces and, therefore, some guidance on how the proteins interact with eukaryotic cells.

The purified YP_106315.1 protein (SEQ ID NO: 6) was found to stimulate RAW 267 macrophage cell lines to produce actin tails. In comparing FIG. 12a with FIGS. 12b and 12c, substantial cell structural changes were found to occur, including increased actin formation and multinucleation. This result was surprising. The protein under investigation was found to stimulate phenotypic changes in macrophage cell lines. The amino acid sequence of the protein (SEQ ID NO: 6) has an inositol polyphosphate kinase domain which may be important for the phenotype described above. As such, this protein and, therefore, rHlpme may be attractive drug targets. That is, given that YP_106315.1, and by analogy rHlpme, has been found to transform macrophage cell lines in the manner described above, agents that block or otherwise interfere with these proteins would be useful as preventive or therapeutic agents for *Burkholderia* infection. Thus, the invention further comprises the use of an agent that blocks or interferes with the action of YP_106315.1 (SEQ ID NO: 6) and rHlpme (SEQ ID NO: 4) for preventing of treating *Burkholderia* infection. For example, such agent may be a YP_106315.1 (SEQ ID NO: 6) or rHlpme (SEQ ID NO: 4) receptor antagonist.

EXAMPLE 3

Antibody Study

Materials and Methods
a) Polyclonal Antisera Generation

Polyclonal antisera was prepared in the manner described above. As discussed above, the ability of antibodies to detect the bacteria in an indirect ELISA using polyclonal antisera from groups of 5 mice vaccinated with rHlpme adjuvant was assessed. The data is shown in FIG. 7 (as means of triplicates).

b) Western Blotting of Mouse Tissue Homogenates and Detection with wFHA-1B5 mAb

Tissue homogenates from infected (*B. pseudomallei*) and uninfected mice were run on a 4-12% Bis-Tris NuPage polyacrylamide gel (Invitrogen) in MOPS SDS buffer according to manufacture's recommendations. Resolved proteins were blotted onto nitrocellulose paper using a wet or semi-dry apparatus (Biorad) as recommended by the manufacturer. Following protein transfer, membranes were probed with wFHA-1B5 mouse monoclonal antibody (mAb was generated by SACRI Antibody Services) using SNAP i.d. (vacuum filtration) protein detection system (Millipore). Briefly, the membrane was assembled in the blot holder and blocked with SuperBlock+0.1% tween 20. A vacuum was applied until all blocking buffer was pulled through the membrane. The membrane was then incubated with wFHA-1B5 mAb diluted 1:200 in blocking buffer. After a 10 minute incubation, the vacuum was applied as above. Membranes were then washed 3× in PBST (PBS+T (0.05% Tween 20) and incubated with HRP-conjugated goat anti-mouse IgG diluted 1:5000 in blocking buffer for 10 minutes before applying the vacuum. Membranes were washed 3× in PBST and 1× in PBS followed by 5 minute incubation with SuperSignal West Pico chemiluminescent substrate (Pierce).

Figure 13:
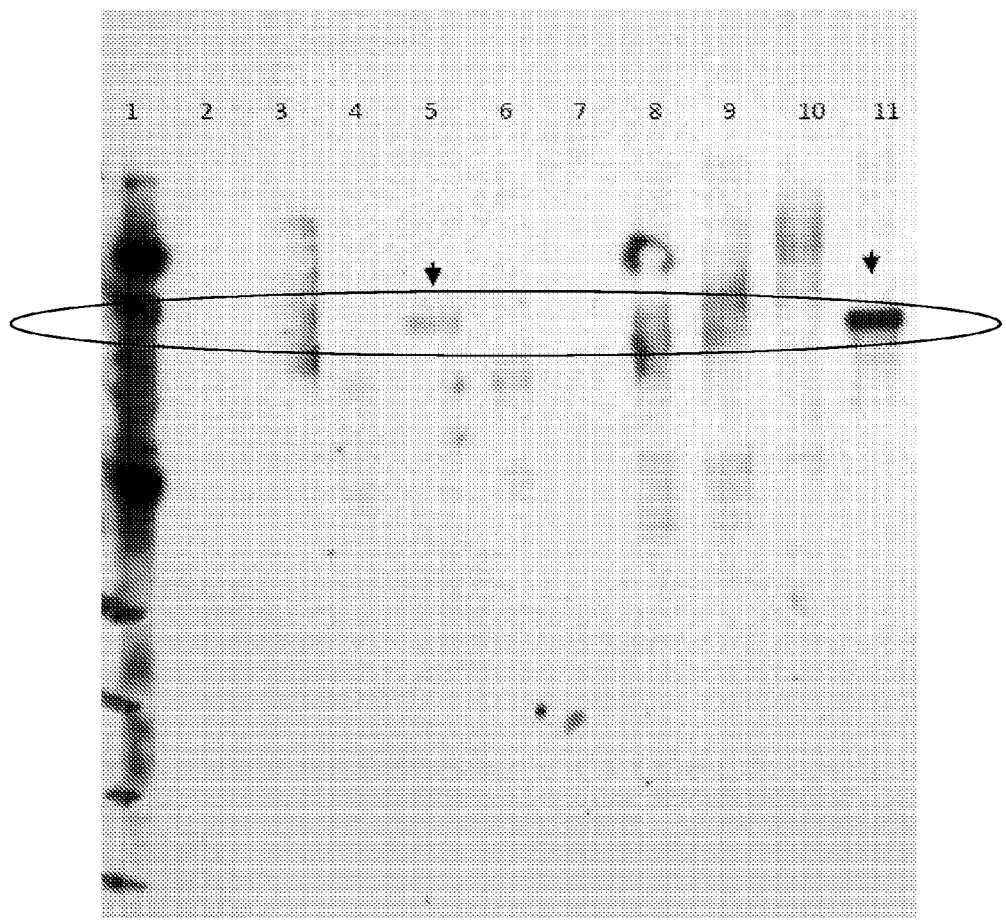
FIG. 13 illustrates the Western blot of mouse tissue homogenates treated with wFHA-185 monoclonal antibody, as discussed in Example 3.

FIG. 13 illustrates the Western blot of the mouse tissue homogenates, wherein: lane 1=PageRuler MWM; lane 2=spleen; lane 3=liver; lane 4=lungs; lane 5=brain; lane 6=*B. pseudomallei* colony; lane 7=*B. mallei* colony; lane 8=spleen; lane 9=lungs; lane 10=brain; lane 11=protein (heparin purified). Lane 2-5 were tissues from infected mice while 8-10 were from uninfected mice. The arrow (↓) identifies the protein in question and an oval has been added to further highlight the bands.

Results and Discussion

It is first noted that the protein YP_106315.1 (SEQ ID NO: 6) is expressed in *Burkholderia pseudomallei* infected mouse brain tissue but not in appreciable amount in the liver, lung, spleen (FIG. 13). It is also noted that the monoclonal antibody for the protein (SEQ ID NO: 6) specifically identifies the recombinant protein and the protein in infected mouse tissue (FIG. 13). As discussed above, polyclonal sera was found to react with live whole cells of *B. mallei* and *B. pseudomallei* (FIG. 7).

The above example illustrates the generation of monoclonal antibodies (mAbs) raised against YP_106315.1 (SEQ ID NO: 6). The generation of polyclonal antibodies has been described earlier above. It will be understood that antibodies (mono- and polyclonal) can also be raised against rHlpme (SEQ ID NO: 4).

Although the invention has been described with reference to certain specific embodiments, various modifications thereof will be apparent to those skilled in the art without departing from the purpose and scope of the invention as outlined in the claims appended hereto. Any examples provided herein are included solely for the purpose of illustrating the invention and are not intended to limit the invention in any way. Any drawings provided herein are solely for the purpose of illustrating various aspects of the invention and are not intended to be drawn to scale or to limit the invention in any way. The disclosures of all prior art recited herein are incorporated herein by reference in their entirety.

We claim:

1. An isolated antibody specific to a polypeptide having the amino acid sequence of SEQ ID NO: 4 or SEQ ID NO: 6.

2. The antibody of claim 1, wherein the antibody is specific to a polypeptide having the amino acid sequence of SEQ ID NO: 4.

3. The antibody of claim 1, wherein the antibody is specific to a polypeptide having the amino acid sequence of SEQ ID NO: 6.

4. The antibody of claim 1, wherein the antibody is polyclonal.

5. The antibody of claim 1, wherein the antibody is monoclonal.

6. The antibody of claim 2, wherein the antibody is polyclonal.

7. The antibody of claim 2, wherein the antibody is monoclonal.

8. The antibody of claim 3, wherein the antibody is polyclonal.

9. The antibody of claim 3, wherein the antibody is monoclonal.

10. A cell line producing the antibody of claim 7.

11. A cell line producing the antibody of claim 9.

* * * * *